US009193666B2

(12) United States Patent
Schaub et al.

(10) Patent No.: US 9,193,666 B2
(45) Date of Patent: *Nov. 24, 2015

(54) PROCESS FOR PREPARING ALKANOLAMINES BY HOMOGENEOUSLY CATALYZED ALCOHOL AMINATION

(75) Inventors: Thomas Schaub, Neustadt (DE); Boris Buschhaus, Mannheim (DE); Marion Kristina Brinks, Mannheim (DE); Mathias Schelwies, Heidelberg (DE); Rocco Paciello, Bad Duerkheim (DE); Johann-Peter Melder, Boehl-Iggelheim (DE); Martin Merger, Frankenthal (DE)

(73) Assignee: BASF SE, Ludwigshafen (DE)

( * ) Notice: Subject to any disclaimer, the term of this patent is extended or adjusted under 35 U.S.C. 154(b) by 178 days.

This patent is subject to a terminal disclaimer.

(21) Appl. No.: 13/415,409

(22) Filed: Mar. 8, 2012

(65) Prior Publication Data
US 2012/0232294 A1    Sep. 13, 2012

Related U.S. Application Data

(60) Provisional application No. 61/450,156, filed on Mar. 8, 2011.

(51) Int. Cl.
| C07C 209/66 | (2006.01) |
| C07F 15/00 | (2006.01) |
| C07C 209/16 | (2006.01) |
| C07C 213/02 | (2006.01) |
| C07D 207/02 | (2006.01) |
| C07D 207/20 | (2006.01) |
| C07D 295/027 | (2006.01) |
| C07D 307/52 | (2006.01) |

(52) U.S. Cl.
CPC ............. *C07C 209/16* (2013.01); *C07C 213/02* (2013.01); *C07D 207/02* (2013.01); *C07D 207/20* (2013.01); *C07D 295/027* (2013.01); *C07D 307/52* (2013.01)

(58) Field of Classification Search
USPC .............................. 564/480; 546/10; 549/492
See application file for complete search history.

(56) References Cited

U.S. PATENT DOCUMENTS

| 4,709,034 | A | 11/1987 | Marsella | |
| 4,855,425 | A | 8/1989 | Marsella | |
| 8,637,709 | B2 * | 1/2014 | Schaub et al. | 564/480 |
| 8,642,811 | B2 | 2/2014 | Baumann et al. | |
| 8,835,691 | B2 | 9/2014 | Klasovsky et al. | |
| 8,927,773 | B2 | 1/2015 | Klasovsky et al. | |
| 2010/0331573 | A1 | 12/2010 | Schaub et al. | |
| 2011/0137029 | A1 | 6/2011 | Kubanek et al. | |
| 2011/0137030 | A1 | 6/2011 | Kubanek et al. | |
| 2011/0152525 | A1 * | 6/2011 | Milstein et al. | 546/10 |
| 2011/0288337 | A1 | 11/2011 | Chedid et al. | |
| 2011/0294977 | A1 | 12/2011 | Schaub et al. | |
| 2012/0004464 | A1 | 1/2012 | Huyghe et al. | |
| 2012/0071692 | A1 | 3/2012 | Ahrens et al. | |
| 2012/0095221 | A1 | 4/2012 | Wigbers et al. | |
| 2012/0157715 | A1 | 6/2012 | Pape et al. | |

FOREIGN PATENT DOCUMENTS

| CA | 1287630 | | 8/1991 |
| DE | 10 2010 040 427 | A1 | 3/2012 |
| EP | 0 234 401 | A1 | 9/1987 |
| EP | 0 239 934 | A2 | 10/1987 |
| JP | 2012-162525 | A | 8/2012 |
| JP | 2013-538816 | A | 10/2013 |
| JP | 2014-505029 | A | 2/2014 |
| JP | 2014-515731 | A | 7/2014 |
| WO | 2010/018570 | | 2/2010 |
| WO | WO 2011/067199 | A1 | 6/2011 |
| WO | WO 2011/067200 | A1 | 6/2011 |
| WO | WO 2011/082967 | A1 | 7/2011 |
| WO | WO 2011/151268 | A1 | 12/2011 |
| WO | WO 2011/157710 | A1 | 12/2011 |
| WO | WO 2012/000952 | A1 | 1/2012 |
| WO | WO 2012/034933 | A1 | 3/2012 |
| WO | WO 2012/049101 | A1 | 4/2012 |

OTHER PUBLICATIONS

U.S. Appl. No. 13/948,736, filed Jul. 23, 2013, Schelwies et al.
U.S. Appl. No. 13/158,667, Wigbers, et al.
U.S. Appl. No. 13/415,466, filed Mar. 8, 2012, Schaub, et al.
U.S. Appl. No. 13/415,412, filed Mar. 8, 2012, Schaub, et al.
U.S. Appl. No. 13/415,174, Mar. 8, 2012, Schaub, et al.
J. A. Marsella, "Homogeneously Catalyzed Synthesis of β-Amino Alcohols and Vicinal Diamines from Ethylene Glycol and 1,2-Propanediol", J. Org. Chem., 52, 1987, pp. 467-468.
Keun-Tae Huh, et al., "Ruthenium Complex Catalyzed Synthesis of Diamino Compounds from ∝, ω-Diols and Secondary Amines", Bull. Kor. Chem. Soc., vol. 11, No. 1, 1990, pp. 45-49.
Natalia Andrushko, et al., "Amination of Aliphatic Alcohols and Diols with an Iridium Pincer Catalyst", ChemCatChem, 2, 2010, pp. 640-643.
Sebastian Bähn, et al., "Ruthenium-catalyzed Selective Monoamination of Vicinal Diols", ChemSusChem, 2, 2009, pp. 551-557.
John A. Marsella, "Ruthenium catalyzed reactions of ethylene glycol with primary amines: steric factors and selectivity control", Journal of Organometallic Chemistry, 407, 1991, pp. 97-105.
Benoit Blank, et al., "Synthesis of Selectively Mono-N-Arylated Aliphatic Diamines via Iridium-Catalyzed Amine Alkylation", Adv. Synth. Catal., 351, 2009, pp. 2903-2911.

(Continued)

Primary Examiner — Charanjit Aulakh
(74) Attorney, Agent, or Firm — Oblon, McClelland, Maier & Neustadt, L.L.P.

(57) ABSTRACT

Process for preparing alkanolamines which have a primary amino group ($-NH_2$) and a hydroxyl group ($-OH$) by alcohol amination of diols having two hydroxyl groups ($-OH$) by means of ammonia with elimination of water, wherein the reaction is carried out homogeneously catalyzed in the presence of at least one complex catalyst comprising at least one element selected from groups 8, 9 and 10 of the Periodic Table and also at least one donor ligand.

12 Claims, No Drawings

(56) References Cited

OTHER PUBLICATIONS

G. Jenner, et al., "Ruthenium-catalyzed Synthesis of Piperazines", Journal of Molecular Catalysis, 45, 1988, pp. 165-168.

Young Zoo Youn, et al., "Ruthenium-catalyzed synthesis of 1-substituted-3-hydroxyperhydroazepines", Journal of Molecular Catalysis, 79, 1993, pp. 39-45.

K.I. Fujita, et al., "Cp*Ir Complex-Catalyzed Hydrogen Transfer Reactions Directed toward Environmentally Benign Organic Synthesis", Synlett, No. 4, 2005, pp. 560-571.

Ken-ichi Fujita, et al., "Cp*Ir Complex-Catalyzed N-Heterocyclization of Primary Amines with Diols: A New Catalytic System for Environmentally Benign Synthesis of Cyclic Amines", Organic Letters, vol. 6, No. 20, 2004, pp. 3525-3528.

Ken-ichi Fujita, et al., "Oxidative Cyclization of Amino Alcohols Catalyzed by a Cp*Ir Complex. Synthesis of Indoles, 1,2,3,4-Tetrahydroquinolines, and 2,3,4,5-Tetrahydro-1-benzazepine", Organic Letters, vol. 4, No. 16, 2002, pp. 2691-2694.

Ainara Nova, et al., "An Experimental-Theoretical Study of the Factors that Affect the Switch between Ruthenium-Catalyzed Dehydrogenative Amide Formation versus Amine Alkylation", Organometallics, DOI: 10.1021/om101015u, 2010, pp. 6548-6558.

M. Haniti S. A. Hamid, et al., "Ruthenium-Catalyzed N-Alkylation of Amines and Sulfonamides Using Borrowing Hydrogen Methodology", J. Am. Chem. Soc., 131, 2009, pp. 1766-1774.

Ourida Saidi, et al., "Borrowing Hydrogen in Water and Ionic Liquids: Iridium-Catalyzed Alkylation of Amines with Alcohols", Organic Process Research & Development, 14, 2010, pp. 1046-1049.

U.S. Appl. No. 13/516,521, filed Jun. 15, 2012, Maegerlein, et al.

U.S. Appl. No. 14/359,134, filed May 19, 2014, Strautmann, et al.

U.S. Appl. No. 14/357,822, filed May 13, 2014, Strautmann, et al.

International Preliminary Report on Patentability issued Jan. 3, 2012, in Application No. PCT/EP2012/053583.

Annegret Tillack, et al.; "A novel ruthenium-catalyzed animation of primary and secondary alcohols"; Tetrahedron Letters; 47, Nr. 50, Dec. 11, 2006; pp. 8881-8885. XP025003579.

Japanese Office Action issued Oct. 6, 2014 in Patent Application No. 2013-557048 (English Translation only).

\* cited by examiner

PROCESS FOR PREPARING ALKANOLAMINES BY HOMOGENEOUSLY CATALYZED ALCOHOL AMINATION

This patent application claims the benefit of U.S. provisional patent application Ser. No. 61/450,156 filed on Mar. 8, 2011, incorporated in its entirety herein by reference.

The present invention relates to a process for preparing alkanolamines by homogeneously catalyzed alcohol amination of diols by means of ammonia with elimination of water in the presence of a complex catalyst which comprises at least one element selected from groups 8, 9 and 10 of the Periodic Table and also at least one phosphorus donor ligand.

Alkanolamines are compounds which have a primary amino group (—$NH_2$) and a hydroxyl group (—OH).

Alkanolamines are valuable products having many different uses, for example solvents, stabilizers, for the synthesis of chelating agents, as starting materials for the production of synthetic resins, drugs, inhibitors, corrosion inhibitors, polyurethanes, as hardeners for epoxy resins, as surface-active substances and for gas scrubbing.

The amination of diols by means of secondary amines using homogeneous iridium and ruthenium catalysts to form amino alcohols and linear diamines having tertiary amino groups has been described, for example, in EP 239 934; J. A. Marsella, *J. Org. Chem.* 1987, 52, 467-468; U.S. Pat. No. 4,855,425; K.-T. Huh, *Bull. Kor. Chem. Soc.* 1990, 11, 45-49; N. Andrushko, V. Andrushko, P. Roose, K. Moonen, A. Börner, *ChemCatChem,* 2010, 2, 640-643 and S. Bähn, A. Tillack, S. Imm, K. Mevius, D. Michalik, D. Hollmann, L. Neubert, M. Beller, *ChemSusChem* 2009, 2, 551-557. In these studies, the amination is carried out at 100-180° C.

J. A. Marsella, *J. Organomet. Chem.* 1991, 407, 97-105 and B. Blank, S. Michlik, R. Kempe, *Adv. Synth. Catal.* 2009, 351, 2903-2911; G. Jenner, G. Bitsi, *J. Mol. Cat,* 1988, 45, 165-168; Y. Z. Youn, D. Y. Lee, B. W. Woo, J. G. Shim, S. A. Chae, S. C. Shim, *J. Mol. Cat,* 1993, 79, 39-45; K. I. Fujita, R. Yamaguchi, *Synlett,* 2005, 4, 560-571; K. I. Fujii, R. Yamaguchi, *Org. Lett.* 2004, 20, 3525-3528; K. I. Fujita, K. Yamamoto, R. Yamaguchi, *Org. Lett.* 2002, 16, 2691-2694; A. Nova, D. Balcells, N. D. Schley, G. E. Dobereiner, R. H. Crabtree, O. Eisenstein, *Organometallics* DOI: 10.1021/om101015u; and M. H. S. A. Hamid, C. L. Allen, G. W. Lamb, A. C. Maxwell, H. C. Maytum, A. J. A. Watson, J. M. J. Williams, *J. Am. Chem. Soc.* 2009, 131, 1766-1774 and O. Saidi, A. J. Blacker, G. W. Lamb, S. P. Marsden, J. E. Taylor, J. M. J. Williams, *Org. Proc. Res. Dev.* 2010, 14, 1046-1049 describe the amination of diols by means of primary amines using homogeneously dissolved ruthenium- and iridium-based transition metal catalysts. However, the cyclic compounds and not the desired alkanolamines are formed here. The economically attractive amination of diols by means of ammonia to form alkanolamines has not been described for these systems.

EP 0 234 401 A1 describes the reaction of ethylene glycol with ammonia in the presence of a ruthenium carbonyl compound. In the process described in EP 0 234 401 A1, the monoamination product (monoethanolamine) is formed among other things. In addition, large amounts of the secondary and tertiary amines (diethanolamine and triethanolamine) and cyclic products (N-(hydroxyethyl)piperazine and N,N'-bis(hydroxyethyl)piperazine) are formed as by-products.

All the above-described processes for the reaction of diols have the disadvantage that undesired secondary, tertiary and cyclic amines are formed to a major extent in addition to the desired alkanolamines.

It is an object of the present invention to provide a process for preparing alkanolamines by alcohol amination of diols by means of ammonia with elimination of water.

The object is achieved by a process for preparing alkanolamines which have a primary amino group (—$NH_2$) and a hydroxyl group (—OH) by alcohol amination of diols having two hydroxyl groups (—OH) by means of ammonia with elimination of water, wherein the reaction is carried out homogeneously catalyzed in the presence of at least one complex catalyst comprising at least one element selected from groups 8, 9 and 10 of the Periodic Table and also at least one phosphorus donor ligand.

It has surprisingly been found that alkanolamines can be obtained by the homogeneously catalyzed amination of diols by means of ammonia with elimination of water using the complex catalysts which are used in the process of the invention and comprise at least one element selected from groups 8, 9 and 10 of the Periodic Table and also at least one phosphorus donor ligand. The process of the invention has the advantage that it gives alkanolamines in considerably improved yields compared to the processes described in the prior art. In addition, the formation of undesired by-products such as secondary and tertiary amines and also cyclic amines is largely avoided.

Starting Materials

In the process of the invention, starting materials having two hydroxyl groups are used.

Suitable starting materials are virtually all diols which meet the above-mentioned prerequisites. The diols can be straight-chain, branched or cyclic. The alcohols can also bear substituents which are inert under the reaction conditions of the alcohol amination, for example alkoxy, alkenyloxy, alkylamino, dialkylamino and halogens (F, Cl, Br, I).

Suitable starting materials which can be used in the process of the invention are, for example, diols which have a functional group of the formula (—$CH_2$—OH) and a further hydroxyl group (—OH).

In addition, diols having two functional groups of the formula (—$CH_2$—OH) are suitable.

As starting materials, it is possible to use all known diols. Preference is given to diols which have at least one functional group of the formula (—$CH_2$—OH). Greater preference is given to diols which have two functional groups of the formula (—$CH_2$—OH). Examples of diols which can be used as starting materials in the process of the invention are 1,2-ethanediol (ethylene glycol), 1,2-propanediol (1,2-propylene glycol), 1,3-propanediol (1,3-propylene glycol), 1,4-butanediol (1,4-butylene glycol), 1,2-butanediol (1,2-butylene glycol), 2,3-butanediol, 2-methyl-1,3-propanediol, 2,2-dimethyl-1,3-propanediol (neopentyl glycol), 1,5-pentanediol, 1,2-pentanediol, 1,6-hexanediol, 1,2-hexanediol, 1,7-heptanediol, 1,2-heptanediol, 1,8-octanediol, 1,2-octanediol, 1,9-nonanediol, 1,2-nonanediol, 2,4-dimethyl-2,5-hexanediol, the neopentyl glycol ester of hydroxypivalic acid, diethylene glycol, triethylene glycol, 2-butene-1,4-diol, 2-butyne-1,4-diol, polyethylene glycols, polypropylene glycols such as 1,2-polypropylene glycol and 1,3-polypropylene glycol, polytetrahydrofuran, diethanolamine, 1,4-bis(2-hydroxyethyl)piperazine, diisopropanolamine, N-butyldiethanolamine, N-methyldiethanolamine, 1,10-decanediol, 1,12-dodecanediol, 2,5-(dimethanol)-furan and C36-diol (mixture of isomers of alcohols having the empirical formula $C_{36}H_{74}O_2$).

Another name for 2,5-(dimethanol)-furan is 2,5-bis(hydroxymethyl)-furan.

Further suitable starting materials are diols of the general formulae (XXXI), (XXXII) and (XXXIII):

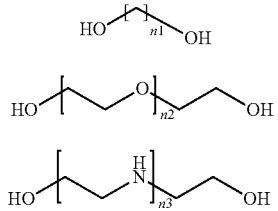

(XXXI)

(XXXII)

(XXXIII)

where n1 is 2-30;

n2 is 1-30 and n3 is 1-30.

Preference is given to diols having two functional groups of the formula (—CH$_2$—OH).

Particularly preferred diols are 1,2-ethanediol (ethylene glycol), 1,2-propanediol (1,2-propylene glycol), 1,3-propanediol (1,3-propylene glycol), 1,4-butanediol (1,4-butylene glycol), 1,2-butanediol (1,2-butylene glycol), 2,3-butanediol, 2-methyl-1,3-propanediol, 2,2-dimethyl-1,3-propanediol (neopentyl glycol), diethylene glycol, triethylene glycol, polyethylene glycols, polypropylene glycols such as 1,2-polypropylene glycol and 1,3-polypropylene glycol, polytetrahydrofuran, 2,5-(dimethanol)-furan and diethanolamine.

Complex Catalyst

In the process of the invention, at least one complex catalyst comprising at least one element selected from groups 8, 9 and 10 of the Periodic Table (IUPAC nomenclature) and also at least one donor ligand is used. The elements of groups 8, 9 and 10 of the Periodic Table comprise iron, cobalt, nickel, ruthenium, rhodium, palladium, osmium, iridium and platinum. Preference is given to complex catalysts which comprise at least one element selected from among ruthenium and iridium.

In one embodiment, the process of the invention is carried out homogeneously catalyzed in the presence of at least one complex catalyst of the general formula (I):

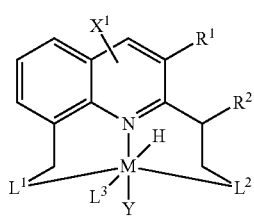

(I)

where

L$^1$ and L$^2$ are each, independently of one another, phosphine (PR$^a$R$^b$), amine (NR$^a$R$^b$), sulfide, SH, sulfoxide (S(=O)R), C$_5$-C$_{10}$-heteroaryl comprising at least one heteroatom selected from among nitrogen (N), oxygen (O) and sulfur (S), arsine (AsR$^a$R$^b$), stibane (SbR$^a$R$^b$) and N-heterocyclic carbenes of the formula (II) or (III):

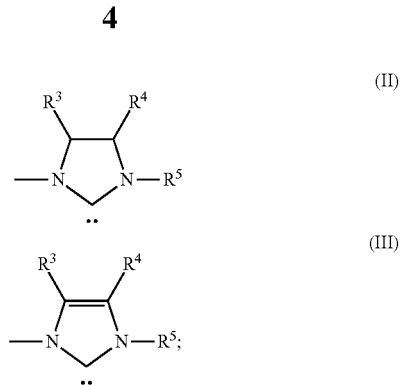

(II)

(III)

L$^3$ is a monodentate two-electron donor selected from the group consisting of carbon monoxide (CO), PR$^a$R$^b$R$^c$, NO$^+$, AsR$^a$R$^b$R$^c$, SbR$^a$R$^b$R$^c$, SR$^a$R$^b$, nitrile (RCN), isonitrile (RNC), nitrogen (N$_2$), phosphorus trifluoride (PF$_3$), carbon monosulfide (CS), pyridine, thiophene, tetrahydrothiophene and N-heterocyclic carbenes of the formula (II) or (III);

R$^1$ and R$^2$ are both hydrogen or together with the carbon atoms to which they are bound form a phenyl ring which together with the quinolinyl unit of the formula I forms an acridinyl unit;

R, R$^a$, R$^b$, R$^c$, R$^3$, R$^4$ and R$^5$ are each, independently of one another, unsubstituted or at least monosubstituted C$_1$-C$_{10}$-cycloalkyl, C$_3$-C$_{10}$-heterocyclyl comprising at least one heteroatom selected from among N, O and S, C$_5$-C$_{10}$-aryl or C$_5$-C$_{10}$-heteroaryl comprising at least one heteroatom selected from among N, O and S, where the substituents are selected from the group consisting of: F, Cl, Br, OH, CN, NH$_2$ and C$_1$-C$_{10}$-alkyl;

Y is a monoanionic ligand selected from the group consisting of H, F, Cl, Br, I, OCOR, OCOCF$_3$, OSO$_2$R, OSO$_2$CF$_3$, CN, OH, OR and N(R)$_2$ or an uncharged molecule selected from the group consisting of NH$_3$, N(R)$_3$ and R$_2$NSO$_2$R;

X$^1$ represents one, two, three, four, five, six or seven substituents on one or more atoms of the acridinyl unit or one, two, three, four or five substituents on one or more atoms of the quinolinyl unit, where the radicals X$^1$ are selected independently from the group consisting of hydrogen, F, Cl, Br, I, OH, NH$_2$, NO$_2$, —NC(O)R, C(O)NR$_2$, —OC(O)R, —C(O)OR, CN and borane derivatives which can be obtained from the catalyst of the formula I by reaction with NaBH$_4$ and unsubstituted or at least monosubstituted C$_1$-C$_{10}$-alkoxy, C$_1$-C$_{10}$-alkyl, C$_3$-C$_{10}$-cycloalkyl, C$_3$-C$_{10}$-heterocyclyl comprising at least one heteroatom selected from among N, O and S, C$_5$-C$_{10}$-aryl and C$_5$-C$_{10}$-heteroaryl comprising at least one heteroatom selected from among N, O and S, where the substitutents are selected from the group consisting of: F, Cl, Br, OH, CN, NH$_2$ and C$_1$-C$_{10}$-alkyl; and M is iron, cobalt, nickel, ruthenium, rhodium, palladium, osmium, iridium or platinum.

It should be pointed out here that the complex catalyst of the formula (I) bears a positive charge when Y is an uncharged molecule selected from the group consisting of NH$_3$, NR$_3$, R$_2$NSO$_2$R and M is selected from the group consisting of ruthenium, nickel, palladium and iron.

In a preferred embodiment, the process of the invention is carried out in the presence of at least one homogeneously dissolved complex catalyst of the formula (I), where the substituents have the following meanings:

$L^1$ and $L^2$, are each, independently of one another, $PR^aR^b$, $NR^aR^b$, sulfide, SH, S(=O)R, $C_5$-$C_{10}$-heteroaryl comprising at least one heteroatom selected from among N, O and S;

$L^3$ is a monodentate two-electron donor selected from the group consisting of CO, $PR^aR^bR^c$, $NO^+$, RCN, RNC, $N_2$, $PF_3$, CS, pyridine, thiophene and tetrahydrothiophene;

$R^1$ and $R^2$ are both hydrogen or together with the carbon atoms to which they are bound form a phenyl ring which together with the quinolinyl unit of the formula (I) forms an acridinyl unit;

R, $R^a$, $R^b$, $R^c$, $R^3$, $R^4$ and $R^5$ are each, independently of one another, unsubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl or $C_5$-$C_{10}$-heteroaryl comprising at least one heteroatom selected from among N, O and S;

Y is a monoanionic ligand selected from the group consisting of H, F, Cl, Br, OCOR, $OCOCF_3$, $OSO_2R$, $OSO_2CF_3$, CN, OH, OR and $N(R)_2$;

$X^1$ represents one, two, three, four, five, six or seven substituents on one or more atoms of the acridinyl unit or one, two, three, four or five substituents on one or more atoms of the quinolinyl unit, where $X^1$ is selected independently from the group consisting of hydrogen, F, Cl, Br, I, OH, $NH_2$, $NO_2$, —NC(O)R, $C(O)NR_2$, —OC(O)R, —C(O)OR, CN and borane derivatives which can be obtained from the catalyst of the formula (I) by reaction with $NaBH_4$ and unsubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl and $C_5$-$C_{10}$-heteroaryl comprising at least one heteroatom selected from among N, O and S;

and

M is ruthenium or iridium.

In a further preferred embodiment, the process of the invention is carried out in the presence of at least one homogeneously dissolved complex catalyst where $R^1$ and $R^2$ are both hydrogen and the complex catalyst is a catalyst of the formula (IV):

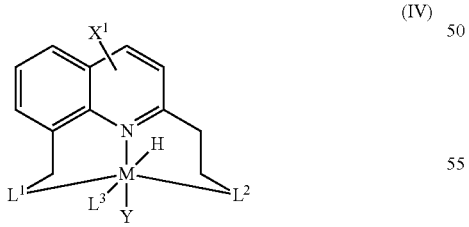

(IV)

and $X^1$, $L^1$, $L^2$, $L^3$ and Y are as defined above.

In a further preferred embodiment, the process of the invention is carried out in the presence of at least one homogeneously dissolved complex catalyst where $R^1$ and $R^2$ together with the carbon atoms to which they are bound form a phenyl ring which together with the quinolinyl unit of the formula (I) forms an acridinyl unit and the complex catalyst is a catalyst of the formula (V):

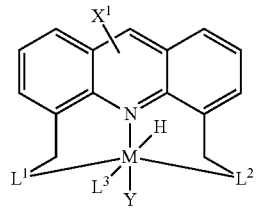

(V)

and $X^1$, $L^1$, $L^2$, $L^3$ and Y are as defined above.

Some complex catalysts (formulae (VI), (VII), (VIII), (IX), (X), (XI), (XII) and (XIII)) which can be used in the process of the invention are shown by way of example below:

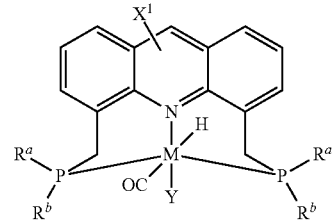

(VI)

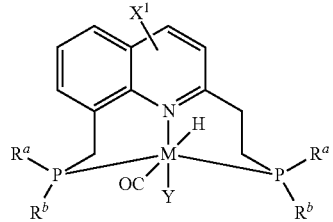

(VII)

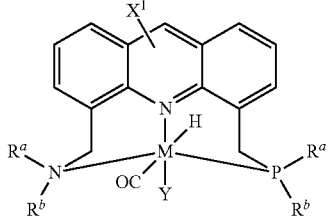

(VIII)

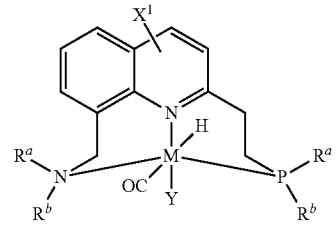

(IX)

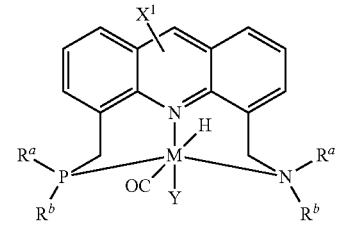

(X)

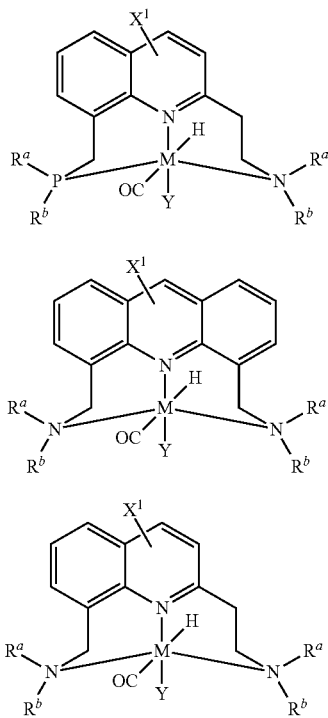

In a further preferred embodiment, the process of the invention is carried out in the presence of at least one complex catalyst selected from the group of catalysts of the formulae (VI), (VII), (VIII), (IX), (X), (XI), (XII) and (XIII), where $R^a$ and $R^b$ are each, independently of one another, unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

Y is a monoanionic ligand selected from the group consisting of H, F, Cl, Br, OCOR, $OCOCF_3$, $OSO_2R$, $OSO_2CF_3$, CN, OH, OR, $N(R)_2$;

R is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl, $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

$X^1$ represents one, two or three substituents on one or more atoms of the acridinyl unit or one or two substituents on one or more atoms of the quinolinyl unit, where the radicals $X^1$ are selected independently from the group consisting of hydrogen, F, Cl, Br, I, OH, $NH_2$, $NO_2$, —NC(O)R, C(O)$NR_2$, —OC(O)R, —C(O)OR, CN and borane derivatives which can be obtained from the catalyst of the formula I by reaction with $NaBH_4$ and unsubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl and $C_5$-$C_{10}$-heteroaryl comprising at least one heteroatom selected from among N, O and S;

and

M is ruthenium or iridium.

In a further preferred embodiment, the process of the invention is carried out in the presence of at least one complex catalyst selected from the group consisting of catalysts of the formulae (VI), (VII), (VIII), (IX), (X), (XI), (XII) and (XIII), where $R^a$ and $R^b$ are each, independently of one another, methyl, ethyl, isopropyl, tert-butyl, cyclohexyl, cyclopentyl, phenyl or mesityl;

Y is a monoanionic ligand selected from the group consisting of H, F, Cl, Br, $OCOCH_3$, $OCOCF_3$, $OSO_2CF_3$, CN and OH;

$X^1$ is a substituent on an atom of the acridinyl unit or a substituent on an atom of the quinolinyl unit, where $X^1$ is selected from the group consisting of hydrogen, F, Cl, Br, OH, $NH_2$, $NO_2$, —NC(O)R, C(O)$NR_2$, —OC(O)R, —C(O)OR, CN and borane derivatives which can be obtained from the catalyst of the formula (I) by reaction with $NaBH_4$ and unsubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl and $C_5$-$C_{10}$-heteroaryl comprising at least one heteroatom selected from among N, O and S;

M is ruthenium or iridium.

In a further preferred embodiment, the process of the invention is carried out in the presence of at least one complex catalyst from the group consisting of the catalysts of the formulae (VI), (VII), (VIII), (IX), (X), (XI), (XII) and (XIII), where $R^a$ and $R^b$ are each, independently of one another, methyl, ethyl, isopropyl, tert-butyl, cyclohexyl, cyclopentyl, phenyl or mesityl;

Y is a monoanionic ligand selected from the group consisting of H, F, Cl, Br, I, $OCOCH_3$, $OCOCF_3$, $OSO_2CF_3$, CN and OH;

$X^1$ is hydrogen;

and

M is ruthenium or iridium.

In a particularly preferred embodiment, $L^3$ is carbon monoxide (CO).

In a particularly preferred embodiment, the process of the invention is carried out in the presence of a complex catalyst of the formula (XIVa):

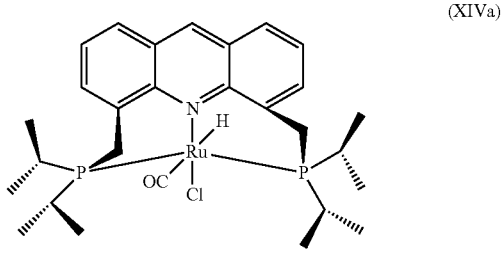

In a very particularly preferred embodiment, the process of the invention is carried out in the presence of a complex catalyst of the formula (XIVb):

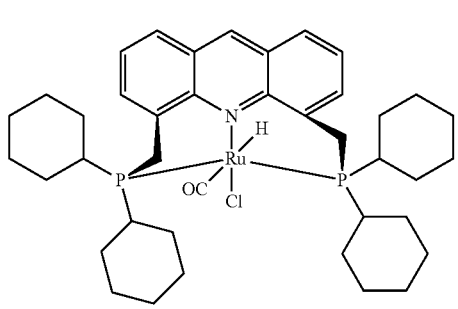

(XIVb)

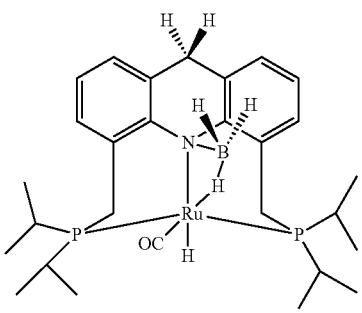

(XVI)

In a further particularly preferred embodiment, the process of the invention is carried out in the presence of at least one homogeneously dissolved complex catalyst of the formula (XV) in which $R^1$, $R^2$, $R^3$, $L^2$ and $L^3$ are as defined above.

The borane derivative of the formula XVI can be obtained according to the following reaction equation:

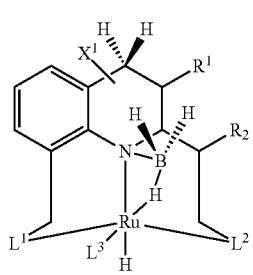

(XV)

Complex catalysts of the formula (XV) can be obtained by reacting catalysts of the formula (I) with sodium borohydride ($NaBH_4$). The reaction proceeds according to the general reaction equation:

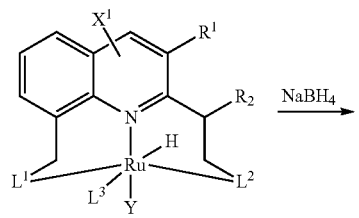

In a further embodiment, the process of the invention is carried out using at least one complex catalyst comprising at least one element selected from groups 8, 9 and 10 of the Periodic Table (IUPAC nomenclature) and also at least one phosphorus donor ligand of the general formula (XXI),

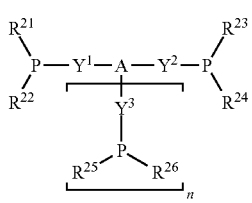

(XXI)

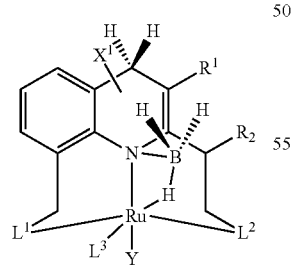

where
n is 0 or 1;
$R^{21}$, $R^{22}$, $R^{23}$, $R^{24}$, $R^{25}$, $R^{26}$ are each, independently of one another, unsubstituted or at least monosubstituted $C_1$-$C_{10}$-alkyl, $C_1$-$C_4$-alkyldiphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from among N, O and S, $C_5$-$C_{14}$-aryl or $C_5$-$C_{10}$-heteroaryl comprising at least one heteroatom selected from among N, O and S, In a further particularly preferred embodiment, the process of the invention is carried out in the presence of a complex catalyst of the formula (XVI):

where the substituents are selected from the group consisting of: F, Cl, Br, OH, CN, $NH_2$ and $C_1$-$C_{10}$-alkyl;

A is i) a bridging group selected from the group consisting of unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from among N, O and S, $C_5$-$C_{14}$-aromatic and $C_5$-$C_6$-heteroaromatic comprising at least one heteroatom selected from among N, O and S, where the substituents are selected from the group consisting of: $C_1$-$C_4$-alkyl, phenyl, F, Cl, Br, OH, $OR^{27}$, $NH_2$, $NHR^{27}$ and $N(R^{27})_2$, where $R^{27}$ is selected from among $C_1$-$C_{10}$-alkyl and $C_5$-$C_{10}$-aryl;

or ii) a bridging group of the formula (XXII) or (XXIII):

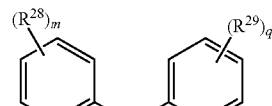
(XXII)

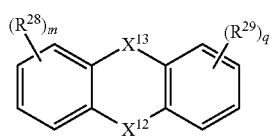
(XXIII)

m, q are each, independently of one another, 0, 1, 2, 3 or 4;

$R^{28}$, $R^{29}$ are selected independently from the group consisting of $C_1$-$C_{10}$-alkyl, F, Cl, Br, OH, $OR^{27}$, $NH_2$, $NHR^{27}$ and $N(R^{27})_2$, where $R^{27}$ is selected from among $C_1$-$C_{10}$-alkyl and $C_5$-$C_{10}$-aryl;

$X^{11}$, $X^{12}$ are each, independently of one another, NH, O or S;

$X^{13}$ is a bond, NH, $NR^{30}$, O, S or $CR^{31}R^{32}$, $R^{30}$ is unsubstituted or at least monosubstituted $C_1$-$C_{10}$ alkyl, $C_3$-$C_{10}$-cycloalkyl, $C_3$-$C_{10}$-heterocyclyl comprising at least one heteroatom selected from among N, O and S, $C_5$-$C_{14}$-aryl or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

$R^{31}$, $R^{32}$ are each, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from among N, O and S, $C_5$-$C_{14}$-aryl, $C_5$-$C_{14}$-aryloxy or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

$Y^1$, $Y^2$, $Y^3$, are each, independently of one another, a bond, unsubstituted or at least monosubstituted methylene, ethylene, trimethylene, tetramethylene, pentamethylene or hexamethylene, where the substituents are selected from the group consisting of: F, Cl, Br, OH, $OR^{27}$, CN, $NH_2$, $NHR^{27}$, $N(R^{27})_2$ and $C_1$-$C_{10}$-alkyl, where $R^{27}$ is selected from among $C_1$-$C_{10}$-alkyl and $C_5$-$C_{10}$-aryl.

According to the invention, A is a bridging group. When A is selected from the group consisting of unsubstituted or at least monosubstituted $C_1$-$C_6$-alkane, $C_3$-$C_{10}$-cycloalkane, $C_3$-$C_{10}$-heterocycloalkane, $C_5$-$C_{14}$-aromatic and $C_5$-$C_6$-heteroaromatic and bridging groups of the formula (II) or (III), two hydrogen atoms of the bridging group are replaced by bonds to the adjacent substituents $Y^1$ and $Y^2$ when n=0. When n=1, three hydrogen atoms of the bridging group are replaced by three bonds to the adjacent substituents $Y^1$, $Y^2$ and $Y^3$.

When A is P (phosphorus), the phosphorus forms two bonds to the adjacent substituents $Y^1$ and $Y^2$ and one bond to a substituent selected from the group consisting of $C_1$-$C_4$-alkyl and phenyl when n=0. When n=1, the phosphorus forms three bonds to the adjacent substituents $Y^1$, $Y^2$ and $Y^3$.

When A is N (nitrogen), the nitrogen forms two bonds to the adjacent substituents $Y^1$ and $Y^2$ and one bond to a substituent selected from the group consisting of $C_1$-$C_4$-alkyl and phenyl when n=0. When n=1, the nitrogen forms three bonds to the adjacent substituents $Y^1$, $Y^2$ and $Y^3$.

When A is O (oxygen), n=0. The oxygen forms two bonds to the adjacent substituents $Y^1$ and $Y^2$.

Preference is given to complex catalysts which comprise at least one element selected from among ruthenium and iridium.

In a preferred embodiment, the process of the invention is carried out in the presence of at least one complex catalyst comprising at least one element selected from groups 8, 9 and 10 of the Periodic Table and also at least one phosphorus donor ligand of the general formula (XXI), where n is 0 or 1;

$R^{21}$, $R^{22}$, $R^{23}$, $R^{24}$, $R^{25}$, $R^{26}$ are each, independently of one another, unsubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{14}$-aryl or $C_5$-$C_{10}$-heteroaryl comprising at least one heteroatom selected from among N, O and S;

A is i) a bridging group selected from the group consisting of unsubstituted $C_1$-$C_6$-alkane, $C_3$-$C_{10}$-cycloalkane, $C_3$-$C_{10}$-heterocycloalkane comprising at least one heteroatom selected from among N, O and S, $C_5$-$C_{14}$-aromatic and $C_5$-$C_6$-heteroaromatic comprising at least one heteroatom selected from among N, O and S;

or ii) a bridging group of the formula (XXII) or (XXIII):

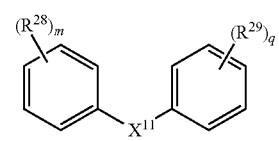
(XXII)

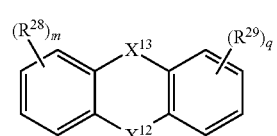
(XXIII)

m, q are each, independently of one another, 0, 1, 2, 3 or 4;

$R^{28}$, $R^{29}$ are selected independently from the group consisting of $C_1$-$C_{10}$-alkyl, F, Cl, Br, OH, $OR^{27}$, $NH_2$, $NHR^{27}$ and $N(R^{27})_2$, where $R^{27}$ is selected from among $C_1$-$C_{10}$-alkyl and $C_5$-$C_{10}$-aryl;

$X^{11}$, $X^{12}$ are each, independently of one another, NH, O or S;

$X^{13}$ is a bond, NH, $NR^{30}$, O, S or $CR^{31}R^{32}$;

$R^{30}$ is unsubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{14}$-aryl or $C_5$-$C_{10}$-heteroaryl comprising at least one heteroatom selected from among N, O and S;

$R^{31}$, $R^{32}$ are each, independently of one another, unsubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from among N, O and S, $C_5$-$C_{14}$-aryl, $C_5$-$C_{14}$-aryloxy or $C_5$-$C_{10}$-heteroaryl comprising at least one heteroatom selected from among N, O and S;

$Y^1$, $Y^2$, $Y^3$, are each, independently of one another, a bond, unsubstituted methylene, ethylene, trimethylene, tetramethylene, pentamethylene or hexamethylene.

In a further preferred embodiment, the process of the invention is carried out in the presence of at least one complex catalyst comprising at least one element selected from groups 8, 9 and 10 of the Periodic Table and also at least one phosphorus donor ligand of the general formula (XXV),

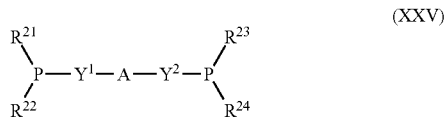

(XXV)

where $R^{21}$, $R^{22}$, $R^{23}$, $R^{24}$ are each, independently of one another, unsubstituted or at least monosubstituted $C_1$-$C_{10}$-alkyl, $C_1$-$C_4$-alkyldiphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from among N, O and S, $C_5$-$C_{14}$-aryl or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

A is i) a bridging group selected from the group consisting of unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from among N, O and S, $C_5$-$C_{14}$-aromatic and $C_5$-$C_6$-heteroaromatic comprising at least one heteroatom selected from among N, O and S, where the substituents are selected from the group consisting of: $C_1$-$C_4$-alkyl, phenyl, F, Cl, Br, OH, $OR^{27}$, $NH_2$, $NHR^{27}$ or $N(R^{27})_2$, where $R^{27}$ is selected from among $C_1$-$C_{10}$-alkyl and $C_5$-$C_{10}$-aryl;

or ii) a bridging group of the formula (XXII) or (XXIII):

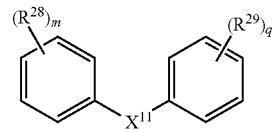

(XXII)

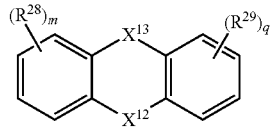

(XXIII)

m, q are each, independently of one another, 0, 1, 2, 3 or 4;

$R^{28}$, $R^{29}$ are selected independently from the group consisting of $C_1$-$C_{10}$-alkyl, F, Cl, Br, OH, $OR^{27}$, $NH_2$, $NHR^{27}$ and $N(R^{27})_2$, where $R^{27}$ is selected from among $C_1$-$C_{10}$-alkyl and $C_5$-$C_{10}$-aryl;

$X^{11}$, $X^{12}$ are each, independently of one another, NH, O or S, $X^{13}$ is a bond, NH, $NR^{30}$, O, S or $CR^{31}R^{32}$;

$R^{30}$ is unsubstituted or at least monosubstituted $C_3$-$C_{10}$-cycloalkyl, $C_3$-$C_{10}$-heterocyclyl comprising at least one heteroatom selected from among N, O and S, $C_5$-$C_{14}$-aryl or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

$R^{31}$, $R^{32}$ are each, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from among N, O and S, $C_5$-$C_{14}$-aryl, $C_5$-$C_{14}$-aryloxy or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

$Y^1$, $Y^2$ are each, independently of one another, a bond, unsubstituted or at least monosubstituted methylene, ethylene, trimethylene, tetramethylene, pentamethylene or hexamethylene, where the substituents are selected from the group consisting of: F, Cl, Br, OH, $OR^{27}$, CN, $NH_2$, $NHR^{27}$, $N(R^{27})_2$ and $C_1$-$C_{10}$-alkyl, where $R^{27}$ is selected from among $C_1$-$C_{10}$-alkyl and $C_5$-$C_{10}$-aryl.

In a further preferred embodiment, the process of the invention is carried out in the presence of at least one complex catalyst comprising at least one element selected from groups 8, 9 and 10 of the Periodic Table and also at least one phosphorus donor ligand of the general formula (XXVI),

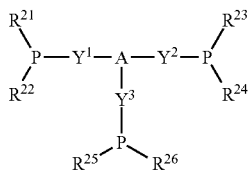
(XXVI)

where
R²¹, R²², R²³, R²⁴, R²⁵, R²⁶ are each, independently of one another, unsubstituted or at least monosubstituted $C_1$-$C_{10}$-alkyl, $C_1$-$C_4$-alkyldiphenylphosphine, $C_3$-$C_{10}$-cycloalkyl, $C_3$-$C_{10}$-heterocyclyl comprising at least one heteroatom selected from among N, O and S, $C_5$-$C_{14}$-aryl or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

A is a bridging group selected from the group consisting of unsubstituted or at least monosubstituted N, P, $C_1$-$C_6$-alkane, $C_3$-$C_{10}$-cycloalkane, $C_3$-$C_{10}$-heterocycloalkane comprising at least one heteroatom selected from among N, O and S, $C_5$-$C_{14}$-aromatic and $C_5$-$C_6$-heteroaromatic comprising at least one heteroatom selected from among N, O and S, where the substituents are selected from the group consisting of: $C_1$-$C_4$-alkyl, phenyl, F, Cl, Br, OH, $OR^{27}$, $NH_2$, $NHR^{27}$ and $N(R^{27})_2$, where $R^{27}$ is selected from among $C_1$-$C_{10}$-alkyl and $C_5$-$C_{10}$-aryl;

$Y^1, Y^2, Y^3$ are each, independently of one another, a bond, unsubstituted or at least monosubstituted methylene, ethylene, trimethylene, tetramethylene, pentamethylene or hexamethylene, where the substituents are selected from the group consisting of: F, Cl, Br, OH, $OR^{27}$, CN, $NH_2$, $NHR^{27}$, $N(R^{27})_2$ and $C_1$-$C_{10}$-alkyl, where $R^{27}$ is selected from among $C_1$-$C_{10}$-alkyl and $C_5$-$C_{10}$-aryl.

In a further preferred embodiment, the process of the invention is carried out in the presence of at least one complex catalyst comprising at least one element selected from groups 8, 9 and 10 of the Periodic Table and also at least one phosphorus donor ligand of the general formula (XXV), where R²¹, R²², R²³, R²⁴ are each, independently of one another, methyl, ethyl, isopropyl, tert-butyl, cyclopentyl, cyclohexyl, phenyl, or mesityl;

A is
i) a bridging group selected from the group consisting of methane, ethane, propane, butane, cyclohexane, benzene, naphthalene and anthracene;
or
ii) a bridging group of the formula (XXVII) or (XXVIII):

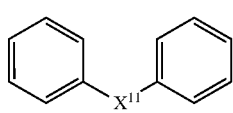
(XXVII)

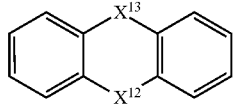
(XXVIII)

$X^{11}, X^{12}$ are each, independently of one another, NH, O or S;
$X^{13}$ is a bond, NH, O, S or $CR^{31}R^{32}$;
$R^{31}, R^{32}$ are each, independently of one another, unsubstituted $C_1$-$C_{10}$-alkyl;
$Y^1, Y^2$ are each, independently of one another, a bond, methylene or ethylene.

In a particularly preferred embodiment, the process of the invention is carried out in the presence of at least one complex catalyst comprising at least one element selected from groups 8, 9 and 10 of the Periodic Table and also at least one phosphorus donor ligand of the general formula (XXIX) or (XXX),

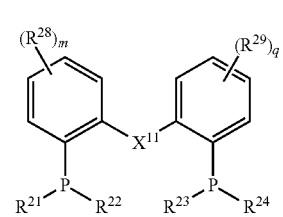
(XXIX)

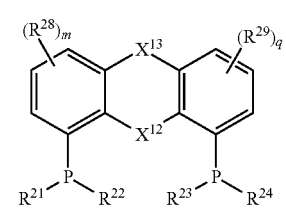
(XXX)

where the abovementioned definitions and preferences apply to m, q, $R^{21}$, $R^{22}$, $R^{23}$, $R^{24}$, $R^{28}$, $R^{29}$, $X^{19}$, $X^{12}$ and $X^{13}$.

In a further particularly preferred embodiment, the process of the invention is carried out in the presence of at least one complex catalyst comprising at least one element selected from the group consisting of ruthenium and iridium and also at least one phosphorus donor ligand selected from the group consisting of 1,2-bis(diphenylphosphino)ethane (dppe), 1,3-bis(diphenylphosphino)propane (dppp), 1,4-bis(diphenylphosphino)butane (dppb), 2,3-bis(dicyclohexylphosphino)ethane (dcpe), 4,5-bis(diphenylphosphino)-9,9-dimethylxanthene (xantphos), 1,1,1-tris(diethylphosphinomethyl)ethane (rhodaphos), bis(2-diphenylphosphinoethyl)phenylphosphine and 1,1,1-tris(diphenylphosphinomethyl)-ethane (triphos).

In a further particularly preferred embodiment, the process of the invention is carried out in the presence of a complex catalyst comprising ruthenium and also at least one phosphorus donor ligand selected from the group consisting of 4,5-bis(diphenylphosphino)-9,9-dimethylxanthene (xantphos), bis(2-diphenylphosphino-ethyl)phenylphosphine and 1,1,1-tris(diphenylphosphinomethyl)ethane (triphos).

In a further particularly preferred embodiment, the process of the invention is carried out in the presence of a complex catalyst comprising iridium and also at least one phosphorus donor ligand selected from the group consisting of 4,5-bis (diphenylphosphino)-9,9-dimethylxanthene (xantphos), bis(2-diphenylphosphino-ethyl)phenylphosphine and 1,1,1-tris(diphenylphosphinomethyl)ethane (triphos).

For the purposes of the present invention, the term $C_1$-$C_{10}$-alkyl refers to branched, unbranched, saturated and unsaturated groups. Preference is given to alkyl groups having from 1 to 6 carbon atoms ($C_1$-$C_6$-alkyl). Greater preference is given to alkyl groups having from 1 to 4 carbon atoms ($C_1$-$C_4$-alkyl).

Examples of saturated alkyl groups are methyl, ethyl, n-propyl, isopropyl, n-butyl, isobutyl, sec-butyl, tert-butyl, amyl and hexyl.

Examples of unsaturated alkyl groups (alkenyl, alkynyl) are vinyl, allyl, butenyl, ethynyl and propynyl.

The $C_1$-$C_{10}$-alkyl group can be unsubstituted or substituted by one or more substituents selected from the group consisting of F, Cl, Br, hydroxy (OH), $C_1$-$C_{10}$-alkoxy, $C_5$-$C_{10}$-aryloxy, $C_5$-$C_{10}$-alkylaryloxy, $C_5$-$C_{10}$-heteroaryloxy comprising at least one heteroatom selected from among N, O, S, oxo, $C_3$-$C_{10}$-cycloalkyl, phenyl, $C_5$-$C_{10}$-heteroaryl comprising at least one heteroatom selected from among N, O, S, $C_5$-$C_{10}$-heterocyclyl comprising at least one heteroatom selected from among N, O, S, naphthyl, amino, $C_1$-$C_{10}$-alkylamino, $C_5$-$C_{10}$-arylamino, $C_5$-$C_{10}$-heteroarylamino comprising at least one heteroatom selected from among N, O, S, $C_1$-$C_{10}$-dialkylamino, $C_{10}$-$C_{12}$-diarylamino, $C_{10}$-$C_{20}$-alkylarylamino, $C_1$-$C_{10}$-acyl, $C_1$-$C_{10}$-acyloxy, $NO_2$, $C_1$-$C_{10}$-carboxy, carbamoyl, carboxamide, cyano, sulfonyl, sulfonylamino, sulfinyl, sulfinylamino, thiol, alkylthiol, $C_5$-$C_{10}$-arylthiol and $C_1$-$C_{10}$-alkylsulfonyl.

The above definition of $C_1$-$C_{10}$-alkyl applies analogously to $C_1$-$C_{30}$-alkyl and to $C_1$-$C_6$-alkane.

For the present purposes, the term $C_3$-$C_{10}$-cycloalkyl refers to saturated, unsaturated monocyclic and polycyclic groups. Examples of $C_3$-$C_{10}$-cycloalkyl are cyclopropyl, cyclobutyl, cyclopentyl, cyclohexyl or cycloheptyl. The cycloalkyl groups can be unsubstituted or substituted by one or more substituents as have been defined above for the $C_1$-$C_{10}$-alkyl group.

The abovementioned definition of $C_3$-$C_{10}$-cycloalkyl applies analogously to $C_3$-$C_{10}$-cycloalkane.

Alcohol Amination

The homogeneous catalysts can be produced either directly in their active form or only under the reaction conditions from customary precursors with addition of the appropriate ligands. Customary precursors are, for example, [Ru(p-cymene)$Cl_2$]$_2$, [Ru(benzene)$Cl_2$]$_n$, [Ru(CO)$_2Cl_2$]$_n$, [Ru(CO)$_3Cl_2$]$_2$ [Ru(COD)(allyl)], [Ru$Cl_3$*$H_2O$], [Ru(acetylacetonate)$_3$], [Ru(DMSO)$_4Cl_2$], [Ru(PPh$_3$)$_3$(CO)(H)Cl], [Ru(PPh$_3$)$_3$(CO)$Cl_2$], [Ru(PPh$_3$)$_3$(CO)(H)$_2$], [Ru(PPh$_3$)$_3$$Cl_2$], [Ru(cyclopentadienyl)(PPh$_3$)$_2$Cl], [Ru(cyclopentadienyl)(CO)$_2$Cl], [Ru(cyclopentadienyl)(CO)$_2$H], [Ru(cyclopentadienyl)(CO)$_2$]$_2$, [Ru(pentamethylcyclopentadienyl)(CO)$_2$]$_2$, [Ru(penta-methylcylcopentadienyl)(CO)$_2$H], [Ru(pentamethylcyclopentadienyl)(CO)$_2$]$_2$, [Ru(indenyl)(CO)$_2$Cl], [Ru(indenyl)(CO)$_2$H], [Ru(indenyl)(CO)$_2$]$_2$, ruthenocene, [Ru(binap)$Cl_2$], [Ru(bipyridine)$_2Cl_2$*2$H_2O$], [Ru(COD)$Cl_2$]$_2$, [Ru(pentamethylcyclopentadienyl)(COD)Cl], [Ru$_3$(CO)$_{12}$], [Ru(tetraphenylhydroxycyclopentadienyl)(CO)$_2$H], [Ru(PMe$_3$)$_4$(H)$_2$], [Ru(PEt$_3$)$_4$(H)$_2$], [Ru(PnPr$_3$)$_4$(H)$_2$], [Ru(PnBu$_3$)$_4$(H)$_2$], [Ru(PnOctyl$_3$)$_4$(H)$_2$], [Ir$Cl_3$*$H_2O$], KIr$Cl_4$, $K_3$Ir$Cl_6$, [Ir(COD)Cl]$_2$, [Ir(cyclooctene)$_2$Cl]$_2$, [Ir(ethene)$_2$Cl]$_2$, [Ir(cyclopentadienyl)$Cl_2$]$_2$, [Ir(pentamethylcyclopentadienyl)$Cl_2$]$_2$, [Ir(cylopentadienyl)(CO)$_2$], [Ir(pentamethylcyclopentadienyl)(CO)$_2$], [Ir(PPh$_3$)$_2$(CO)(H)], [Ir(PPh$_3$)$_2$(CO)(Cl)], [Ir(PPh$_3$)$_3$(Cl)].

For the purposes of the present invention, homogeneously catalyzed means that the catalytically active part of the complex catalyst is at least partly present in solution in the liquid reaction medium. In a preferred embodiment, at least 90% of the complex catalyst used in the process is present in solution in the liquid reaction medium, more preferably at least 95%, particularly preferably more than 99%; the complex catalyst is most preferably entirely present in solution in the liquid reaction medium (100%), in each case based on the total amount in the liquid reaction medium.

The amount of the metal component of the catalyst, preferably ruthenium or iridium, is generally from 0.1 to 5000 ppm by weight, in each case based on the total liquid reaction medium.

The reaction occurs in the liquid phase, generally at a temperature of from 20 to 250° C. The process of the invention is preferably carried out at temperatures in the range from 100° C. to 200° C., particularly preferably in the range from 110 to 160° C.

The reaction can generally be carried out at a total pressure of from 0.1 to 20 MPa absolute, which can be either the autogenous pressure of the solvent at the reaction temperature or the pressure of a gas such as nitrogen, argon or hydrogen. The process of the invention is preferably carried out at a total pressure in the range from 0.2 to 15 MPa absolute, particularly preferably at a total pressure in the range from 1 to 15 MPa absolute.

The average reaction time is generally from 15 minutes to 100 hours.

The aminating agent (ammonia) can be used in stoichiometric, substoichiometric or superstoichiometric amounts based on the hydroxyl groups to be aminated.

In a preferred embodiment, ammonia is used in a from 1- to 250-fold, preferably a from 1- to 100-fold, in particular in a from 1.5- to 10-fold, molar excess per mole of hydroxyl groups to be reacted in the starting material. Higher excesses of ammonia are also possible. The ammonia can be introduced in gaseous form, liquid form or as a solution in the solvent or starting material.

The process of the invention can be carried out either in a solvent or without solvent. Suitable solvents are polar and nonpolar solvents which can be used in pure form or in mixtures. For example, it is possible to use only one nonpolar or one polar solvent in the process of the invention. It is also possible to use mixtures of two or more polar solvents or mixtures of two or more nonpolar solvents or mixtures of one or more polar solvents with one or more nonpolar solvents. The product can also be used as solvent, either in pure form or in mixtures with polar or nonpolar solvents.

Suitable nonpolar solvents are, for example, saturated and unsaturated hydrocarbons such as hexane, heptane, octane, cyclohexane, benzene, toluene, xylene and mesitylene and linear and cyclic ethers such as THF, diethyl ether, 1,4-dioxane, MTBE (tert-butyl methyl ether), diglyme and 1,2-dimethoxyethane. Preference is given to using toluene, xylene or mesitylene.

Suitable polar solvents are, for example, water, dimethylformamide, formamide, tert-amylalcohol and acetonitrile. Preference is given to using water. The water can either be added before the reaction, be formed as water of reaction during the reaction or be added after the reaction in addition to the water of reaction. A further preferred solvent is tert-amylalcohol.

To carry out the reaction in the liquid phase, ammonia, the diol optionally together with one or more solvents, together with the complex catalyst are introduced into a reactor. The introduction of ammonia, diol, optionally solvent and complex catalyst can be carried out simultaneously or separately. The reaction can be carried out continuously, in the semibatch mode, in the batch mode, admixed in product as solvent or without admixing in a single pass.

It is in principle possible to use all reactors which are basically suitable for gas/liquid reactions at the given temperature and the given pressure for the process of the invention. Suitable standard reactors for gas/liquid reaction systems and for liquid/liquid reaction systems are, for example, indicated in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, chapter 3.3 "Reactors for gas-liquid reactions". Examples which may be mentioned are stirred tank reactors, tube reactors or bubble column reactors.

In the amination reaction, a hydroxyl group, preferably a primary hydroxyl group (—CH$_2$—OH), of the starting material is reacted with ammonia to form a primary amino group (—NH$_2$), with in each case one mole of water of reaction being formed per mole of reacted hydroxyl group.

The reaction of 1,2-ethylene glycol leads, for example, to the corresponding 2-aminoethanol.

The reaction output formed in the reaction generally comprises the corresponding alkanolamines, the one or more solvents if used, the complex catalyst, possibly unreacted starting materials and ammonia and also the water of reaction formed.

Any excess ammonia present, any solvent present, the complex catalyst and the water of reaction are removed from the reaction output. The amination product obtained can be worked up further. The excess ammonia, the complex catalyst, any solvent or solvents and any unreacted starting materials can be recirculated to the amination reaction.

If the amination reaction is carried out without solvent, the homogeneous complex catalyst is dissolved in the product after the reaction. This can remain in the product or be separated off therefrom by a suitable method. Possibilities for separating off the catalyst are, for example, scrubbing with a solvent which is not miscible with the product and in which the catalyst dissolves better than in the product as a result of a suitable choice of the ligands. The catalyst concentration in the product is optionally reduced by multistage extraction. As extractant, preference is given to using a solvent which is also suitable for the target reaction, e.g. toluene, benzene, xylenes, alkanes such as hexanes, heptanes and octanes and acyclic or cyclic ethers such as diethyl ether and tetrahydrofuran, which can after concentration by evaporation be reused together with the extracted catalyst for the reaction. It is also possible to remove the catalyst by means of a suitable absorbent. The catalyst can also be separated off by adding water to the product phase if the reaction is carried out in a solvent which is immiscible with water. If the catalyst in this case dissolves preferentially in the solvent, it can be separated off with the solvent from the aqueous product phase and optionally be reused. This can be brought about by selection of suitable ligands. The resulting aqueous diamines, triamines or polyamines can be used directly as technical-grade amine solutions. It is also possible to separate the amination product from the catalyst by distillation.

If the reaction is carried out in a solvent, the latter can be miscible with the amination product and be separated off by distillation after the reaction. It is also possible to use solvents which have a miscibility gap with the amination products or the starting materials. Suitable solvents for this purpose are, for example, toluene, benzene, xylenes, alkanes such as hexanes, heptanes and octanes and acyclic or cyclic ethers such as diethyl ether, tetrahydrofuran and dioxane. As a result of suitable choice of the phosphine ligands, the catalyst preferentially dissolves in the solvent phase. The phosphine ligands can also be selected so that the catalyst dissolves in the amination product. In this case, the amination product can be separated from the catalyst by distillation.

The solvent can also be miscible with the starting materials and the product under the reaction conditions and only form a second liquid phase comprising the major part of the catalyst after cooling. As solvents which display this property, mention may be made by way of example of toluene, benzene, xylenes, alkanes such as hexanes, heptanes and octanes. The catalyst can then be separated off together with the solvent and be reused. The product phase can also be admixed with water in this variant. The proportion of the catalyst comprised in the product can subsequently be separated off by means of suitable absorbents such as polyacrylic acid and salts thereof, sulfonated polystyrenes and salts thereof, activated carbons, montmorillonites, bentonites and zeolites or else be left in the product.

The amination reaction can also be carried out in a two-phase system. In the case of the two-phase reaction, suitable nonpolar solvents are, in particular, toluene, benzene, xylenes, alkanes such as hexanes, heptanes and octanes in combination with lipophilic phosphine ligands on the transition metal catalyst, as a result of which the transition metal catalyst accumulates in the nonpolar phase. In this embodiment, in which the product and the water of reaction and any unreacted starting materials form a second phase enriched with these compounds the major part of the catalyst can be separated off from the product phase by simple phase separation and be reused.

If volatile by-products or unreacted starting materials or the water formed in the reaction or added after the reaction to aid the extraction are undesirable, they can be separated off from the product without problems by distillation.

It can also be advantageous for the water formed in the reaction to be removed continuously from the reaction mixture. The water of reaction can be separated off from the reaction mixture directly by distillation or as azeotrope with addition of a suitable solvent (entrainer) and using a water separator or be removed by addition of water-withdrawing auxiliaries.

The addition of bases can have a positive effect on product formation. Suitable bases which may be mentioned here are alkali metal hydroxides, alkaline earth metal hydroxides, alkaline metal alkoxides, alkaline earth metal alkoxides, alkali metal carbonates and alkaline earth metal carbonates, which can be used in amounts of from 0.01 to 100 molar equivalents based on the metal catalyst used.

The present invention further provides for the use of a complex catalyst comprising at least one element selected from groups 8, 9 and 10 of the Periodic Table and also at least one donor ligand for the homogeneously catalyzed preparation of alkanolamines which have a primary amino group (—NH$_2$) and a hydroxyl group (—OH) by alcohol amination of diols having two hydroxyl groups (—OH) by means of ammonia.

In a preferred embodiment, the present invention provides for the use of a homogeneously dissolved complex catalyst of the general formula (I):

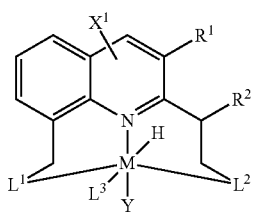

(I)

where
L¹ and L² are each, independently of one another, PR$^a$R$^b$, NR$^a$R$^b$, sulfide, SH, S(=O)R, C$_5$-C$_{10}$-heteroaryl comprising at least one heteroatom selected from among N, O and S, AsR$^a$R$^b$, SbR$^a$R$^b$ and N-heterocyclic carbenes of the formula (II) or (III):

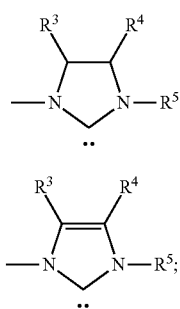

(II)

(III)

L³ is a monodentate two-electron donor selected from the group consisting of CO, PR$^a$R$^b$R$^c$, NO$^+$, AsR$^a$R$^b$R$^c$, SbR$^a$R$^b$R$^c$, SR$^a$R$^b$, RCN, RNC, N$_2$, PF$_3$, CS, pyridine, thiophene, tetrahydrothiophene and N-heterocyclic carbenes of the formula (II) or (III);

R¹ and R² are both hydrogen or together with the carbon atoms to which they are bound form a phenyl ring which together with the quinolinyl unit of the formula (I) forms an acridinyl unit;

R, R$^a$, R$^b$, R$^c$, R³, R⁴, and R⁵ are each, independently of one another, unsubstituted or at least monosubstituted C$_3$-C$_{10}$-cycloalkyl, C$_3$-C$_{10}$-heterocyclyl comprising at least one heteroatom selected from among N, O and S, C$_5$-C$_{10}$-aryl or C$_5$-C$_{10}$-heteroaryl comprising at least one heteroatom selected from among N, O and S,
where the substituents are selected from the group consisting of: F, Cl, Br, OH, CN, NH$_2$ and C$_1$-C$_{10}$-alkyl;

Y is a monoanionic ligand selected from the group consisting of H, F, Cl, Br, I, OCOR, OCOCF$_3$, OSO$_2$R, OSO$_2$CF$_3$, CN, OH, OR and N(R)$_2$ or an uncharged molecule selected from the group consisting of NH$_3$, N(R)$_3$ and R$_2$NSO$_2$R;

X¹ represents one, two, three, four, five, six or seven substituents on one or more atoms of the acridinyl unit or one, two, three, four or five substituents on one or more atoms of the quinolinyl unit,
where the radicals X¹ are selected independently from the group consisting of hydrogen, F, Cl, Br, I, OH, NH$_2$, NO$_2$, —NC(O)R, C(O)NR$_2$, —OC(O)R, —C(O)OR, CN and borane derivatives which can be obtained from the catalyst of the formula I by reaction with NaBH$_4$ and unsubstituted or at least monosubstituted C$_1$-C$_{10}$-alkoxy, C$_1$-C$_{10}$-alkyl, C$_3$-C$_{10}$-cycloalkyl, C$_3$-C$_{10}$-heterocyclyl comprising at least one heteroatom selected from among N, O and S, C$_5$-C$_{10}$-aryl and C$_5$-C$_{10}$-heteroaryl comprising at least one heteroatom selected from among N, O and S,
where the substituents are selected from the group consisting of: F, Cl, Br, OH, CN, NH$_2$ and C$_1$-C$_{10}$-alkyl; and M is iron, cobalt, nickel, ruthenium, rhodium, palladium, osmium, iridium or platinum, for the homogeneously catalyzed preparation of alkanolamines which have a primary amino group (—NH$_2$) and a hydroxyl group (—OH) by alcohol amination of diols having two hydroxy groups (—OH) by means of ammonia, where the definitions and preferences described above for the process of the invention apply to the catalyst of the general formula (I).

In a further preferred embodiment, the present invention relates to the use of a homogeneously dissolved complex catalyst of the general formula (XV):

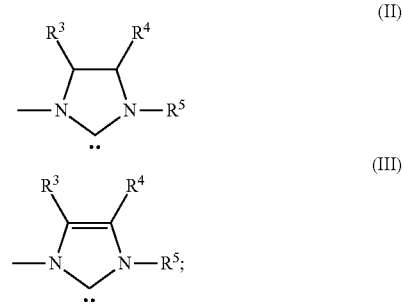

(XV)

where
L¹ and L² are each, independently of one another, PR$^a$R$^b$, NR$^a$R$^b$, sulfide, SH, S(=O)R, C$_5$-C$_{10}$-heteroaryl comprising at least one heteroatom selected from among N, O and S, AsR$^a$R$^b$, SbR$^a$R$^b$ or N-heterocyclic carbenes of the formula (II) or (III):

(II)

(III)

L³ is a monodentate two-electron donor selected from the group consisting of CO, PR$^a$R$^b$R$^c$, NO$^+$, AsR$^a$R$^b$R$^c$, SbR$^a$R$^b$R$^c$, SR$^a$R$^b$, RCN, RNC, N$_2$, PF$_3$, CS, pyridine, thiophene, tetrahydrothiophene and N-heterocyclic carbenes of the formula (II) or (III);

R¹ and R² are both hydrogen or together with the carbon atoms to which they are bound form a phenyl ring which together with the quinolinyl unit of the formula (I) forms an acridinyl unit;

R, R$^a$, R$^b$, R$^c$, R³, R⁴ and R⁵ are each, independently of one another, unsubstituted or at least monosubstituted C$_1$-C$_{10}$-alkyl, C$_3$-C$_{10}$-cycloalkyl, C$_3$-C$_{10}$-heterocyclyl comprising at least one heteroatom selected from among N, O and S, $C_5$-$C_{10}$-aryl or $C_5$-$C_{10}$-heteroaryl comprising at least one heteroatom selected from among N, O and S,
where the substituents are selected from the group consisting of: F, Cl, Br, OH, CN, $NH_2$ and $C_1$-$C_{10}$-alkyl;

Y is a monoanionic ligand selected from the group consisting of H, F, Cl, Br, I, OCOR, $OCOCF_3$, $OSO_2R$, $OSO_2CF_3$, CN, OH, OR and $N(R)_2$ or uncharged molecules selected from the group consisting of $NH_3$, $N(R)_3$ and $R_2NSO_2R$;

$X^1$ represents one, two, three, four, five, six or seven substituents on one or more atoms of the acridinyl unit or one, two, three, four or five substituents on one or more atoms of the quinolinyl unit,
where the radicals $X^1$ are selected independently from the group consisting of hydrogen, F, Cl, Br, I, OH, $NH_2$, $NO_2$, —NC(O)R, $C(O)NR_2$, —OC(O)R, —C(O)OR, CN and borane derivatives which can be obtained from the catalyst of the formula I by reaction with $NaBH_4$ and unsubstituted or at least monosubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl and $C_5$-$C_{10}$-heteroaryl comprising at least one heteroatom selected from among N, O and S,
where the substituents are selected from the group consisting of: F, Cl, Br, OH, CN, $NH_2$ and $C_1$-$C_{10}$-alkyl; and M is iron, cobalt, nickel, ruthenium, rhodium, palladium, osmium, iridium or platinum, for the homogeneously catalyzed preparation of alkanolamines which have a primary amino group (—$NH_2$) and a hydroxyl group (—OH) by alcohol amination of diols having two hydroxyl groups (—OH) by means of ammonia, where the definitions and preferences described above for the process of the invention apply to the catalyst of the general formula (XV).

The present invention further provides for the use of a complex catalyst comprising at least one element selected from groups 8, 9 and 10 of the Periodic Table and also at least one phosphorus donor ligand of the general formula (XXI),

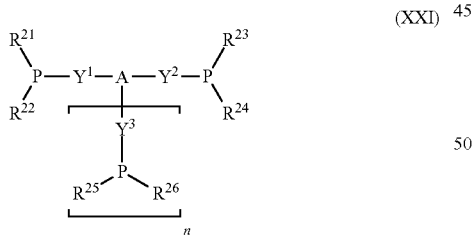

(XXI)

where
n is 0 or 1;
$R^{21}$, $R^{22}$, $R^{23}$, $R^{24}$, $R^{25}$, $R^{26}$ are each, independently of one another, unsubstituted or at least monosubstituted $C_1$-$C_{10}$-alkyl, $C_1$-$C_4$-alkyldiphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from among N, O and S, $C_5$-$C_{14}$-aryl or $C_5$-$C_{10}$-heteroaryl comprising at least one heteroatom selected from among N, O and S,
where the substituents are selected from the group consisting of: F, Cl, Br, OH, CN, $NH_2$ and $C_1$-$C_{10}$-alkyl;

A is
i) a bridging group selected from the group consisting of unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from among N, O and S, $C_5$-$C_{14}$-aromatic and $C_5$-$C_6$-heteroaromatic comprising at least one heteroatom selected from among N, O and S,
where the substituents are selected from the group consisting of: $C_1$-$C_4$-alkyl, phenyl, F, Cl, Br, OH, $OR^{27}$, $NH_2$, $NHR^{27}$ or $N(R^{27})_2$,
where $R^{27}$ is selected from among $C_1$-$C_{10}$-alkyl and $C_5$-$C_{10}$-aryl;
or
ii) a bridging group of the formula (XXII) and (XXIII):

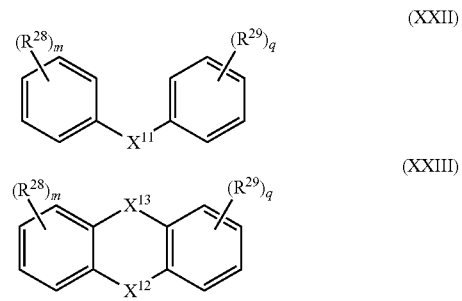

(XXII)

(XXIII)

m, q are each, independently of one another, 0, 1, 2, 3 or 4;
$R^{28}$, $R^{29}$ are selected independently from the group consisting of $C_1$-$C_{10}$-alkyl, F, Cl, Br, OH, $OR^{27}$, $NH_2$, $NHR^{27}$ and $N(R^{27})_2$,
where $R^{27}$ is selected from among $C_1$-$C_{10}$-alkyl and $C_5$-$C_{10}$-aryl;
$X^{11}$, $X^{12}$ are each, independently of one another, NH, O or S;
$X^{13}$ is a bond, NH, $NR^{30}$, O, S or $CR^{31}R^{32}$,
$R^{30}$ is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{14}$-aryl or $C_5$-$C_{10}$-heteroaryl comprising at least one heteroatom selected from among N, O and S,
where the substituents are selected from the group consisting of: F, Cl, Br, OH, CN, $NH_2$ and $C_1$-$C_{10}$-alkyl;
$R^{31}$, $R^{32}$ are each, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from among N, O and S, $C_5$-$C_{14}$-aryl, $C_5$-$C_{14}$-aryloxy or $C_5$-$C_{10}$-heteroaryl comprising at least one heteroatom selected from among N, O and S,
where the substituents are selected from the group consisting of: F, Cl, Br, OH, CN, $NH_2$ and $C_1$-$C_{10}$-alkyl;

$Y^1$, $Y^2$, $Y^3$ are each, independently of one another, a bond, unsubstituted or at least monosubstituted methylene, ethylene, trimethylene, tetramethylene, pentamethylene or hexamethylene,
where the substituents are selected from the group consisting of: F, Cl, Br, OH, $OR^{27}$, CN, $NH_2$, $NHR^{27}$, $N(R^{27})_2$ and $C_1$-$C_{10}$-alkyl,
where $R^{27}$ is selected from among $C_1$-$C_{10}$-alkyl and $C_5$-$C_{10}$-aryl, for the homogeneously catalyzed preparation of alkanolamines which have a primary amino group and a hydroxyl group by alcohol amination of diols having two hydroxyl groups (—OH) by means of ammonia.

The definitions and preferences described for the process of the invention apply to the use of the complex catalyst of the formula (XXI) for the homogeneously catalyzed preparation of alkanolamines which have a primary amino group (—NH$_2$) and a hydroxyl group (—OH) by alcohol amination of diols having two hydroxyl groups (—OH) by means of ammonia.

The invention is illustrated by the following examples without being restricted thereto.

EXAMPLE

General method for the catalytic amination of alcohols by means of ammonia according to the invention Ligand L, metal salt M or catalyst complex XIVb (for preparation, see below, weighed out under an inert atmosphere), solvent and the alcohol to be reacted were placed under an Ar atmosphere in a 160 ml Parr autoclave (stainless steel V4A) having a magnetically coupled inclined blade stirrer (stirring speed: 200-500 revolutions/minute). The indicated amount of ammonia was introduced at room temperature either in precondensed form or directly from the pressurized NH$_3$ gas bottle. If hydrogen was used, this was effected by iterative differential pressure metering. The steel autoclave was electrically heated to the temperature indicated and heated for the time indicated while stirring (500 revolutions/minute) (internal temperature measurement). After cooling to room temperature, venting the autoclave and outgassing the ammonia at atmospheric pressure, the reaction mixture was analyzed by GC (30 m RTX5 amine 0.32 mm 1.5 µm). The results for the amination of 1,4-butanediol (tables 1a, 1b and 2), diethylene glycol (tables 3a, 3b and 4), monoethylene glycol (table 5) and diethanolamine (table 6), 1,5-pentanediol, 1,9-nonanediol, 1,6-hexanediol and 1,10-decanediol (table 7) and 2,5-(dimethanol)-furan (table 8) are given below.

Synthesis of the Catalyst Complex XIVb

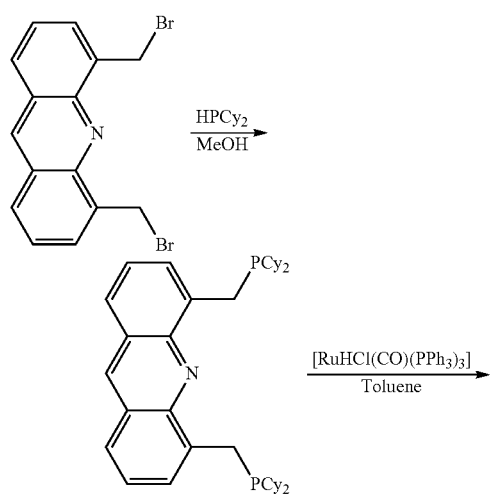

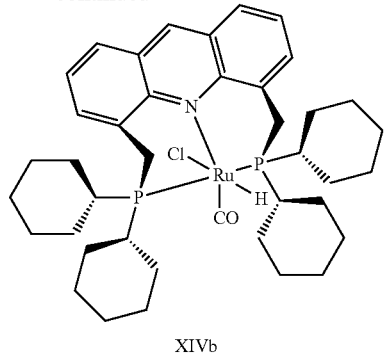

XIVb a) Synthesis of 4,5-bis(dicyclohexylphosphinomethyl)acridine

A solution of 4,5-bis(bromomethyl)acridine[1] (5.2 g, 14.2 mmol) and dicyclohexylphosphine (8.18 g, 36.8 mmol) in 65 ml of anhydrous, degassed methanol was heated at 50° C. under an inert argon atmosphere for 66 hours. After cooling to room temperature, triethylamine (5.72 g, 56.7 mmol) was added and the mixture was stirred for 1 hour. Evaporation of the solvent gave a whitish yellow solid in a red oil. Extraction by means of 3×40 ml of MTBE and concentration of the filtrate gave a reddish brown oil ($^1$H NMR: mixture of product & HPCy$_2$). Taking up in a little warm MTBE followed by addition of ice-cooled methanol resulted in precipitation of a yellow, microcrystalline solid. Oscillation and drying under reduced pressure gave air sensitive 4,5-bis(dicyclohexylphosphinomethyl)acridine (2.74 g, 33%) as a yellow powder.

$^1$H NMR (360.63 MHz, d8-toluene): δ [ppm]=8.07 (s, 1H, H9), 7.91 (d, J=8.3 Hz, 2H, Ar—H), 7.42 (d, J=8.3 Hz, 2H, Ar—H), 7.21 (dd, J=8.3 Hz, J=7.2 Hz, 2H, Ar—H), 3.89 (bs, 4H, —CH$_2$—P), 1.96-1.85 (m, 8H, Cy-H), 1.77-1.54 (m, 20H, Cy-H), 1.26-1.07 (m, 16H, Cy-H). $^{31}$P{$^1$H} NMR (145.98 MHz, d8-toluene): δ [ppm]=2.49 (s, —CH$_2$—P(Cy)$_2$).

b) Synthesis of the Catalyst Complex XIVb 4,5-bis(dicyclohexylphosphinomethyl)acridine (1855 mg, 3.1 mmol) and [RuHCl(CO)(PPh$_3$)$_3$][2] (2678 mg, 2.81 mmol) were heated at 70° C. in 80 ml of degassed toluene for 2 hours. The resulting dark brown solution was evaporated to dryness, the residue was slurried in 3×20 ml of hexane and isolated by filtration. Drying under reduced pressure gave Ru-PNP Pincer complex XIVb (1603 mg, 75%) as an orange-brown powder. $^1$H NMR (360.63 MHz, d8-toluene): δ [ppm]=8.06 (s, 1H, H9), 7.43 (d, J=7.6 Hz, 2H, Ar—H), 7.33 (d, J=6.5 Hz, 2H, Ar—H), 7.06-7.02 (m, 2H, Ar—H), 5.02 (d, J=11.9 Hz, 2H, —CHH—PCy$_2$), 3.54 (d, J=12.2 Hz, 2H, —CHH—PCy$_2$), 2.87 (bs, 2H, —P(C$_a$H(CH$_2$)$_5$)$_2$), 2.54 (bs, 2H, —P(C$_b$H(CH$_2$)$_5$)$_2$), 2.18 (bs, 2H, Cy-H), 1.88-1.85 (m, 8H, Cy-H), 1.65 (bs, 6H, Cy-H), 1.42-1.35 (m, 14H, Cy-H), 1.17-0.82 (m, 12H, Cy-H), −16.29 (t, J=19.1 Hz, 1H, Ru—H). $^{31}$P{$^1$H} NMR (145.98 MHz, d8-toluene): δ [ppm]=60.89 (s, —CH$_2$—P(Cy)$_2$).

[1] J. Chiron, J. P. Galy, *Synlett,* 2003, 15, 2349-2350.
[2] Literature instructions: *Inorganic Syntheses* 1974, 15, 48.
See also: T. Joseph, S. S. Deshpande, S. B. Halligudi, A. Vinu, S. Ernst, M. Hartmann, *J. Mol. Cat. (A)* 2003, 206, 13-21.

| Ligand name | CAS | IUPAC |
|---|---|---|
| Triphos | 22031-12-5 | 1,1,1-tris(diphenylphosphinomethyl)ethane |
| Xantphos | 161265-03-8 | 4,5-bis(diphenylphosphino)-9,9-dimethylxanthene |
| Rhodaphos | 22031-14-7 | 1,1,1-tris(diethylposphinomethyl)ethane |
| DPPEPP | 23582-02-7 | bis(2-diphenylphosphinoethyl)phenylphosphine |
| Tetraphos | 23582-03-8 | tris[2-(diphenylphosphino)ethyl]phosphine |
| dppb | 7688-25-7 | 1,4-Bis(diethylphospino)butane |

TABLE 1a

Amination of 1,4-butanediol using various catalyst systems

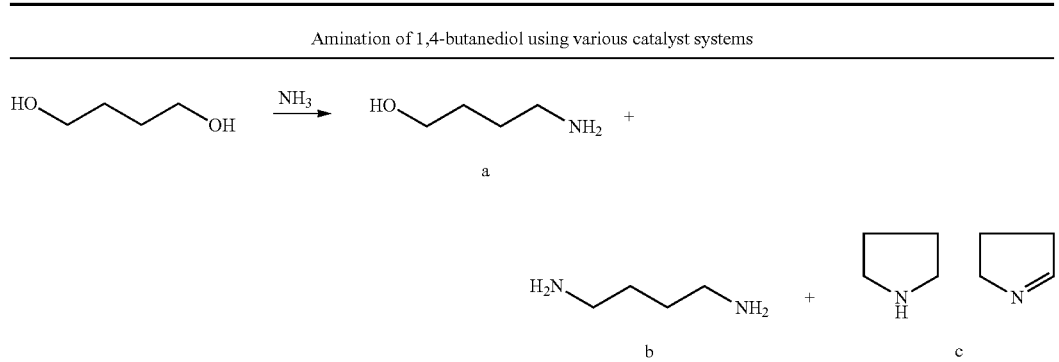

| No. | Solvent[a] | T [°C] | Time [h] | $NH_3$ [eq.][e] | Reaction pressure [bar] | Metal salt [M] | Met. [M] (mol %)[f] | Ligand [L] | Lig. [L] (mol %)[f] | Conversion[b] | Selectivity[c] a:b:c | | |
|---|---|---|---|---|---|---|---|---|---|---|---|---|---|
| 1 | Toluene | 155 | 12 | 6 | 49 | [RuHCl(CO)(PPh$_3$)$_3$] | 0.1 | Triphos | 0.1 | 74.7 | 59.1 | 0.7 | 6.7 |
| 2 | Toluene | 155 | 12 | 6 | 66[d] | [RuHCl(CO)(PPh$_3$)$_3$] | 0.1 | Triphos | 0.1 | 61.8 | 78.0 | 0.6 | 5.4 |
| 3 | Toluene | 155 | 12 | 6 | 45 | [RuHCl(CO)(PPh$_3$)$_3$] | 0.1 | Xantphos | 0.1 | 35.0 | 81.8 | 0.0 | 6.4 |
| 4 | Toluene | 155 | 12 | 6 | 47 | [Ru(COD)methylallyl$_2$] | 0.1 | Tetraphos | 0.1 | 6.0 | 8.5 | 0.0 | 1.6 |
| 5 | Toluene | 155 | 12 | 6 | 39 | [RuHCl(CO)(PPh$_3$)$_3$] | 0.2 | Rhodaphos | 0.2 | 39.8 | 17.5 | 0.0 | 4.6 |
| 6 | Toluene | 155 | 12 | 6 | 38 | [RuHCl(CO)(PPh$_3$)$_3$] | 0.2 | DPPEPP | 0.2 | 66.6 | 68.1 | 0.1 | 11.0 |

[a] 50 ml of solvent; Batch size: 25 mmol of 1,4-butanediol;
[b] Evaluation by GC (% by area);
[c] Product selectivity determined by GC;
[d] Injected cold: 5 bar H$_2$, 8 bar NH$_3$,
[e] Molar equivalents of NH$_3$ per OH function on the substrate;
[f] mol % based on number of OH functions on the substrate

TABLE 1b

Amination of 1,4-butanediol using various catalyst systems

| No | Solvent[a] | T [°C] | Time [h] | $NH_3$ [Eq.][d] | Reaction pressure [bar] | Metall salt [M] | Met. [M] (mol %)[e] | Ligand [L] | Lig. [L] (mol %)[e] | Conversion[b] | Selectivity[c] a: | b: | c |
|---|---|---|---|---|---|---|---|---|---|---|---|---|---|
| 1 | THF | 155 | 12 | 6 | 40 | [RuHCl(CO)(PPh$_3$)$_3$] | 0.2 | dppb | 0.2 | 49.6 | 61.4 | 0.0 | 20.3 |

[a] 50 ml of solvent; Batch size: 25 mmol of 1,4-butanediol;
[b] Evaluation by GC (% by area);
[c] Product selectivity determined by GC;
[d] Molar equivalents of NH$_3$ per OH function on the substrate;
[e] mol % based on number of OH functions on the substrate

TABLE 2

Amination of 1,4-butanediol using XIVb as catalyst system

HO~~~~~~OH  →(NH₃)  HO~~~~~~NH₂  (a)  +  H₂N~~~~~~NH₂ (b)  +  pyrrolidine (c) + 1-pyrroline

| No.[a] | Solvent | T [°C.] | Time [h] | NH₃ [eq.][e] | Reaction pressure [bar] | Further condition | Conversion[b] | Selectivity a | b | c |
|---|---|---|---|---|---|---|---|---|---|---|
| 1 | Toluene | 155 | 12 | 6 | 42 | | 54.6 | 72.2 | 8.8 | 17.7 |
| 2 | Toluene | 155 | 12 | 6 | 41 | 5.0 mol % of water | 63.0 | 71.8 | 9.3 | 17.3 |
| 3 | Toluene | 155 | 12 | 6 | 55 | 5 bar of H₂ injected cold | 25.0 | 81.0 | 4.8 | 13.6 |
| 4 | Toluene | 155 | 12 | 9 | 47 | | 61.1 | 74.2 | 8.9 | 15.7 |
| 5 | p-Xylene | 155 | 12 | 6 | 44 | | 70.6 | 62.6 | 5.8 | 28.7 |
| 6 | p-Xylene | 155 | 12 | 6 | 40 | — | 42.0 | 78.8 | 3.5 | 16.5 |
| 7 | p-Xylene | 155 | 12 | 9 | 48 | | 62.3 | 72.3 | 7.6 | 18.5 |
| 8 | p-Xylene | 155 | 12 | 18 | 78 | | 48.1 | 75.9 | 2.6 | 17.4 |
| 9 | Mesitylene* | 155 | 12 | 6 | 39 | — | 58.3 | 70.5 | 6.7 | 20.3 |

[a] Conditions unless indicated otherwise: 50 ml of solvent, batch size 25 mmol of 1,4-butanediol, 0.1 mol % of catalyst complex XIVb (based on number of OH functions on the substrate),
[b] Evaluation by GC (% by area),
[c] Product selectivity determined by GC,
[e] Molar equivalents of NH₃ per OH function on the substrate

TABLE 3a

Amination of diethylene glycol using various catalyst systems

HO~~~O~~~OH →(NH₃) HO~~~O~~~NH₂ (a) + H₂N~~~O~~~NH₂ (b) + morpholine (c)

| No. | Solvent[a] | T [°C.] | Time [h] | NH₃ [eq.][e] | Reaction pressure [bar] | Metal salt [M] | Met. [M] (mol %)[f] | Ligand [L] | Lig. [L] (mol %)[f] | Conversion[b] | Selectivity[c] a:b:c |
|---|---|---|---|---|---|---|---|---|---|---|---|
| 1 | Toluene | 155 | 12 | 6 | 49 | [RuHCl(CO)(PPh₃)₃] | 0.1 | Triphos | 0.1 | 51.0 | 66.2 0.9 5.9 |
| 2 | Toluene | 155 | 12 | 6 | 59[d] | [RuHCl(CO)(PPh₃)₃] | 0.1 | Triphos | 0.1 | 16.2 | 87.3 0.1 2.3 |
| 3 | Toluene | 180 | 12 | 6 | 43 | [RuHCl(CO)(PPh₃)₃] | 0.2 | Xantphos | 0.1 | 27.7 | 67.1 0.2 5.3 |
| 4 | Toluene | 155 | 12 | 6 | 44 | [Ru(COD)methylallyl₂] | 0.1 | Tetraphos | 0.1 | 3.9 | 0.0 0.0 1.1 |
| 5 | Toluene | 155 | 12 | 6 | 40 | [RuHCl(CO)(PPh₃)₃] | 0.2 | Rhodaphos | 0.2 | 21.8 | 4.7 0.0 1.3 |

[a] 50 ml of solvent; Batch size: 25 mmol of diethylene glycol;
[b] Evaluation by GC (% by area);
[c] Product selectivity determined by GC;
[d] Injected cold: 5 bar of H₂, 8 bar of NH₃;
[e] Molar equivalents of NH₃ per OH function on the substrate;
[f] mol % based on the number of OH functions on the substrate

TABLE 3b

Amination of diethylene glycol using various catalyst systems

HO~~~O~~~OH + NH$_3$ → HO~~~O~~~NH$_2$ (a) + H$_2$N~~~O~~~NH$_2$ (b) + morpholine (c)

| No. | Solvent[a] | T [° C.] | Time [h] | NH$_3$ [eq.][e] | Reaction pressure [bar] | Metal salt [M] | Met. [M] (mol %)[f] | Ligand [L] | Lig. [L] (mol %)[f] | Conversion[b] | Selectivity[c] a:b:c | | |
|---|---|---|---|---|---|---|---|---|---|---|---|---|---|
| 1 | Toluol | 180 | 12 | 6 | 65[d] | [RuHCl(CO)(PPh$_3$)$_3$] | 0.2 | Triphos | 0.2 | 97.6 | 26.4 | 13.4 | 54.0 |
| 2 | Toluol | 155 | 12 | 6 | 40 | [RuHCl(CO)(PPh$_3$)$_3$] | 0.2 | DPPEPP | 0.2 | 21.5 | 46.0 | 0.0 | 2.3 |

[a]50 ml of solvent; Batch size: 25 mmol of diethylene glycol;
[b]Evaluation by GC (% by area);
[c]Product selectivity determined by GC;
[d]Injected cold: 5 bar of H$_2$, 8 bar of NH$_3$;
[e]Molar equivalents of NH$_3$ per OH function on the substrate;
[f]mol % based on the number of OH functions on the substrate

TABLE 4

Amination of diethylene glycol using XIVb as catalyst system

HO~~~O~~~OH + NH$_3$ → HO~~~O~~~NH$_2$ (a) + H$_2$N~~~O~~~NH$_2$ (b) + morpholine (c)

| No.[a] | Solvent | T [° C.] | Time [h] | NH$_3$ [eq.][d] | Reaction pressure [bar] | Further conditions | Conversion[b] | Selectivity[c] a | b | c |
|---|---|---|---|---|---|---|---|---|---|---|
| 1 | Toluene | 135 | 12 | 6 | 38 | | 40.4 | 85.8 | 2.5 | 6.7 |
| 2 | Toluene | 135 | 12 | 6 | 38 | 0.2 mol % of KOtBu | 11.7 | 69.8 | 3.4 | 5.0 |
| 3 | Toluene | 135 | 12 | 6 | 36 | 1 mol % of water | 37.9 | 86.4 | 2.1 | 6.0 |
| 4 | Toluene | 135 | 12 | 6 | 37 | | 42.1 | 87.1 | 3.3 | 6.5 |
| 5 | Toluene | 135 | 12 | 9 | 42 | | 33.8 | 81.4 | 1.5 | 5.5 |
| 6 | Toluene | 135 | 12 | 18 | 57 | | 36.5 | 78.4 | 2.9 | 9.4 |
| 7 | Toluene | 135 | 15 | 1.1 | 9 | | 49.1 | 76.4 | 3.2 | 8.7 |
| 8 | Toluene | 135 | 24 | 6 | 37 | | 60.9 | 75.8 | 9.3 | 8.3 |
| 9 | Toluene | 135 | 60 | 9 | 45 | cat: 0.05 mol % | 28.1 | 81.7 | 6.3 | 2.5 |
| 10 | Toluene | 155 | 12 | 6 | 40 | 5.0 mol % of water | 74.8 | 57.2 | 18.5 | 11.1 |
| 11 | Toluene | 155 | 12 | 6 | 66 | 5 bar of H2 | 61.8 | 69.2 | 18.6 | 8.0 |
| 12 | Toluene | 155 | 12 | 9 | 63 | 5 bar of H2 + 1.0 mol % of water | 55.5 | 72.7 | 16.0 | 6.8 |
| 13 | Toluene | 155 | 12 | 9 | 66 | 5 bar of H2 | 53.1 | 75.0 | 14.1 | 5.8 |
| 14 | p-Xylene | 155 | 12 | 6 | 48 | | 74.4 | 65.8 | 11.5 | 9.5 |
| 15 | p-Xylene | 155 | 12 | 6 | 38 | 1.0 mol % of water | 77.5 | 52.9 | 21.6 | 16.9 |
| 16 | p-Xylene | 155 | 24 | 6 | 53 | 1.0 mol % of water | 84.6 | 51.8 | 20.8 | 12.9 |
| 17 | p-Xylene | 180 | 12 | 6 | 50 | | 100.0 | 0.4 | 46.1 | 27.9 |
| 18 | p-Xylene | 180 | 12 | 6 | 50 | 5 mol % of H2O | 100.0 | 0.4 | 48.2 | 27.4 |

[a]Conditions unless indicated otherwise: 50 ml of solvent, Batch size 25 mmol of diethylene glycol, 0.1 mol % of catalyst complex XIVb (based on number of OH functions on the substrate);
b)Evaluation by GC (% by area);
c)Product selectivity determined by GC;
e)Molar equivalents of NH$_3$ per OH function on the substrate

TABLE 5

Amination of monoethylene glycol using XIVb as catalyst system

HO–CH₂–CH₂–OH + NH₃ → HO–CH₂–CH₂–NH₂ (a) + H₂N–CH₂–CH₂–NH₂ (b) + piperazine (c)

| No.[a] | Solvent | T [°C.] | Time [h] | NH₃ [eq.][d] | Reaction pressure [bar] | Further conditions | Conversion[b] | Selectivity a | b | c |
|---|---|---|---|---|---|---|---|---|---|---|
| 1 | Toluene | 135 | 12 | 6 | 35 | | 14.0 | 68.6 | 16.6 | 0.5 |
| 2 | Toluene | 135 | 12 | 6 | 38 | 0.2 mol % of KOtBu | 39.3 | 65.8 | 18.9 | 0.7 |
| 3 | Toluene | 135 | 12 | 9 | 44 | | 11.0 | 71.9 | 17.5 | 0.7 |
| 4 | Toluene | 135 | 12 | 12 | 48 | | 10.6 | 68.2 | 17.5 | 2.5 |
| 5 | Toluene | 135 | 12 | 18 | 54 | | 13.7 | 69.0 | 15.6 | 2.7 |
| 6 | p-Xylene | 155 | 3 | 6 | 38 | | 18.2 | 56.9 | 19.5 | 1.0 |

[a]Conditions unless indicated otherwise: 50 ml of solvent; Batch size 25 mmol of monoethylene glycol, 0.1 mol % of catalyst complex XIVb (based on number of OH functions on the substrate);
[b]Evaluation by GC (% by area);
[c]Product selectivity determined by GC;
[d]Molar equivalents of NH₃ per OH function on the substrate

TABLE 6

Amination of diethanolamine using XIVb as catalyst system

HO–CH₂CH₂–NH–CH₂CH₂–OH + NH₃ → HO–CH₂CH₂–NH–CH₂CH₂–NH₂ (a) + H₂N–CH₂CH₂–NH–CH₂CH₂–NH₂ (b) + piperazine (c) + H₂N–CH₂CH₂–NH₂ / HO–CH₂CH₂–NH₂ (d)

| No.[a] | Solvent | T [°C.] | Time [h] | NH₃ [eq.][d] | Reaction pressure [bar] | Further conditions | Conversion[b] | Selectivities a | b | c | d |
|---|---|---|---|---|---|---|---|---|---|---|---|
| 1 | Toluene | 135 | 12 | 9 | 43 | | 22.7 | 51.9 | 0.4 | 0.0 | 31.2 |
| 2 | Toluene | 155 | 12 | 6 | 44 | | 49.0 | 41.4 | 1.8 | 0.0 | 30.2 |
| 3 | Toluene | 155 | 24 | 6 | 42 | | 69.0 | 32.6 | 2.1 | 0.0 | 30.6 |
| 4 | Toluene | 155 | 12 | 6 | 45 | | 32.5 | 31.8 | 1.8 | 0.0 | 34.6 |
| 5 | Toluene | 155 | 12 | 9 | 54 | | 57.5 | 47.4 | 2.5 | 4.1 | 34.3 |
| 6 | Toluene | 155 | 12 | 6 | 44 | 1 mol % of KOtBu | 25.7 | 34.8 | 3.3 | 0.0 | 25.3 |
| 7 | Toluene | 155 | 12 | 12 | 57 | | 50.8 | 39.8 | 1.3 | 3.0 | 36.6 |
| 8 | Toluene | 155 | 12 | 6 | 44 | 1 mol % of water | 51.7 | 40.5 | 1.4 | 3.4 | 33.8 |
| 9 | Toluene | 155 | 12 | 6 | 43 | 5 mol % of water | 50.6 | 42.2 | 1.4 | 4.6 | 30.8 |
| 10 | Toluene | 155 | 12 | 6 | 60 | 5 bar of H2 | 33.4 | 51.1 | 1.4 | 4.4 | 30.6 |

[a]Conditions unless indicated otherwise: 50 ml of solvent, Batch size 25 mmol of diethanolamine, 0.1 mol % of catalyst complex XIVb (based on number of OH functions on the substrate);
[b]Evaluation by GC (% by area);
[c]Product selectivity determined by GC;
[d]Molar equivalents of NH₃ per OH function on the substrate

TABLE 7

Amination of (1,5-pentanediol, 1,6-hexanediol, 1,10-decanediol, 1,9-Nonanediol) using various catalyst systems $$HO\diagup\!\!\!\diagup_n\!\!\diagup OH \xrightarrow{NH_3} HO\diagup\!\!\!\diagup_n\!\!\diagup NH_2 \;+\; H_2N\diagup\!\!\!\diagup_n\!\!\diagup NH_2$$
                                                         a                              b

| No.[a] | Substrate | T [°C.] | Time [h] | NH₃ [eq.][e] | Reaction pressure [bar] | Solvent (water-free) | Metall salt [M] | Met. [M] (mol %)[f] | Ligand [L] | Lig. [L] (mol %)[f] | Conversion[b] | Selectivity[c] a:b |
|---|---|---|---|---|---|---|---|---|---|---|---|---|
| 1 | 1,6-Hexanediol | 155 | 12 | 6 | 42 | Toluol | [RuHCl(CO)(PPh₃)₃] | 0.10 | Triphos | 0.10 | 83.0 | 61.3 25.7 |
| 2 | 1,6-Hexanediol | 155 | 12 | 6 | 36 | Toluol | [RuHCl(CO)(PPh₃)₃] | 0.10 | Xantphos | 0.10 | 33.4 | 84.9 4.6 |
| 3 | 1,6-Hexanediol | 155 | 12 | 6 | 40 | Toluol | [RuHCl(CO)(PPh₃)₃] | 0.10 | DPPEPP | 0.10 | 70.7 | 66.5 16.0 |
| 4 | 1,6-Hexanediol | 155 | 12 | 6 | 44 | Toluol | [RuHCl(CO)(PPh₃)₃] | 0.10 | Rhodaphos | 0.10 | 35.1 | 53.0 2.0 |
| 5 | 1,10-Decanediol | 155 | 24 | 6 | 39 | Toluol | [RuHCl(CO)(PPh₃)₃] | 0.20 | Triphos | 0.20 | 85.7 | 43.0 44.4 |
| 7 | 1,5-Pentanediol | 155 | 12 | 6 | 40 | Toluol | [RuHCl(CO)(PPh₃)₃] | 0.10 | Triphos | 0.10 | 70.3 | 66.8 1.3 |
| 8 | 1,5-Pentanediol | 155 | 12 | 6 | 45 | Toluol | [RuHCl(CO)(PPh₃)₃] | 0.10 | DPPEPP | 0.10 | 50.9 | 64.6 7.1 |
| 9[d] | 1,9-Nonanediol | 155 | 24 | 12 | 14 | Mesitylene | [RuHCl(CO)(PPh₃)₃] | 0.20 | Triphos | 0.20 | 79.3 | 54.0 31.1 |

[a] 50 ml of solvent; Batch size: 25 mmol of diol;
[b] Evaluation by GC (% by area);
[c] Product selectivity determined by GC (% by area);
[d] Batch size: 50 mmol of substrate; Batch size: 50 mmol of diol;
[e] Molar equivalents of NH₃ per OH function on the substrate;
[f] mol % based on number of OH functions on the substrate

TABLE 8

Amination of 2,5-dimethanolfuran

| No.[a] | Substrate | T [°C.] | Time [h] | konz. [mol/l] | NH₃ [eq.][d] | Reaction pressure [bar] | Solvent (water-free) | Metall salt [M] | Met. [M] (mol %)[e] | Ligand [L] | Lig. [L] (mol %)[e] | Conversion[b] | Selectivity[c] a:b |
|---|---|---|---|---|---|---|---|---|---|---|---|---|---|
| 1 | 2,5-dimethanolfuran | 140 | 24 | 1 | 6 | 15 | THF | [RuHCl(CO)(PPh₃)₃] | 0.20 | Triphos | 0.20 | 46.8 | 63.1 10.2 |
| 2 | 2,5-dimethanolfuran | 140 | 3 | 0.5 | 6 | 32 | tert-butanol | XIVb | 0.10 | — | — | 84.6 | 49.2 43.6 |

[a] 40 ml of solvent; Batch size: 40 mmol of diol;
[b] Evaluation by GC (% by area);
[c] Product selectivity determined by GC (% by area);
[d] Molar equivalents of NH₃ per OH function on the substrate;
[e] mol % based on number of OH functions on the substrate

The invention claimed is:

1. A process for preparing an alkanolamine comprising a primary amino group (—NH$_2$) and a hydroxyl group (—OH), the process comprising:
aminating a diol comprising two functional groups of formula (—CH$_2$—OH) with ammonia, to eliminate water and obtain the alkanolamine,
wherein the aminating is homogeneously catalyzed in the presence a complex catalyst comprising at least one element selected from groups consisting of 8, 9, and 10 of the Periodic Table, and a donor ligand, wherein the complex catalyst is a catalyst represented by formula (I):

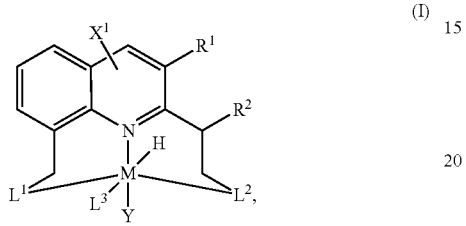

(I)

wherein
L$^1$ and L$^2$ are each independently PR$^a$R$^b$, NR$^a$R$^b$, sulfide, SH, S(=O)R, a C$_5$-C$_{10}$-heteroaryl comprising at least one heteroatom selected from the group consisting of N, O, and S, AsR$^a$R$^b$, SbR$^a$R$^b$, or an N-heterocyclic carbene of formula (II) or (III):

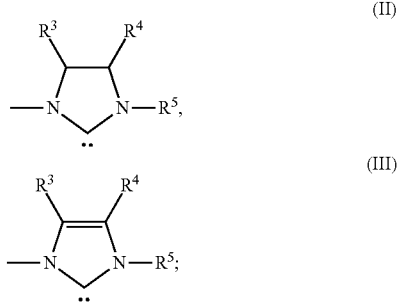

(II)

(III)

L$^3$ is a monodentate two-electron donor selected from the group consisting of CO, PR$^a$R$^b$R$^c$, NO$^+$, AsR$^a$R$^b$R$^c$, SbR$^a$R$^b$R$^c$, SR$^a$R$^b$, RCN, RNC, N$_2$, PF$_3$, CS, pyridine, thiophene, tetrahydrothiophene, and an N-heterocyclic carbene of formula (II) or (III);
R$^1$ and R$^2$ are both hydrogen or together with the carbon atoms to which they are bound form a phenyl ring, which forms an acridinyl unit with the quinolinyl unit of the formula (I);
R, R$^a$, R$^b$, R$^c$, R$^3$, R$^4$ and R$^5$ are each independently an unsubstituted or at least monosubstituted C$_3$-C$_{10}$-cycloalkyl, C$_3$-C$_{10}$-heterocyclyl comprising at least one heteroatom selected from the group consisting of N, O, and S, C$_5$-C$_{10}$-aryl, or C$_5$-C$_{10}$-heteroaryl comprising at least one heteroatom selected from the group consisting of N, O, and S, wherein the substituents are selected from the group consisting of F, Cl, Br, OH, CN, NH$_2$, and a C$_1$-C$_{10}$-alkyl;
Y is a monoanionic ligand selected from the group consisting of H, F, Cl, Br, I, OCOR, OCOCF$_3$, OSO$_2$R, OSO$_2$CF$_3$, CN, OH, OR, and N(R)$_2$, or an uncharged molecule selected from the group consisting of NH$_3$, N(R)$_3$, and R$_2$NSO$_2$R;

X$^1$ is one to seven radical substituents on an atom of the acridinyl unit or one to five radical substituents on an atom of the quinolinyl unit,
wherein the radicals are each independently selected from the group consisting of hydrogen, F, Cl, Br, I, OH, NH$_2$, NO$_2$, —NC(O)R, C(O)NR$_2$, —OC(O)R, —C(O)OR, CN, and a borane derivative obtained by reacting the catalyst of the formula (I) with NaBH$_4$ and an unsubstituted or at least monosubstituted C$_1$-C$_{10}$-alkoxy, C$_1$-C$_{10}$-alkyl, C$_3$-C$_{10}$-cycloalkyl, C$_3$-C$_{10}$-heterocyclyl comprising at least one a heteroatom selected from the group consisting of N, O, and S, C$_5$-C$_{10}$-aryl, and C$_5$-C$_{10}$-heteroaryl comprising at least one a heteroatom selected from the group consisting of N, O, and S, wherein the substituents are selected from the group consisting of F, Cl, Br, OH, CN, NH$_7$, and a C$_1$-C$_{10}$-alkyl; and
M is iron, cobalt, nickel, ruthenium, rhodium, palladium, osmium, iridium, or platinum.

2. The process of claim 1, wherein R$^1$ and R$^2$ are both hydrogen and the complex catalyst is a catalyst of formula (IV):

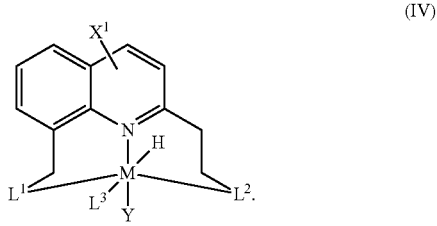

(IV)

3. The process of claim 1, wherein R$^1$ and R$^2$ together with the carbon atoms to which they are bound form a phenyl ring, which forms an acridinyl unit together with the quinolinyl units of the formula (I), and the complex catalyst is a catalyst has a formula (V):

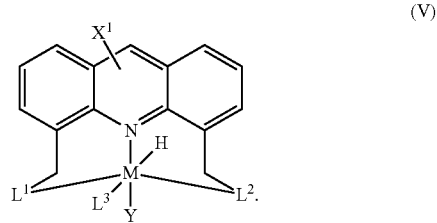

(V)

4. The process of claim 1, wherein the complex catalyst is selected from the group of catalysts of having a formula selected form the group consisting of formulae (VI), (VII), (VIII), (IX), (X), (XI), (XII), and (XIII):

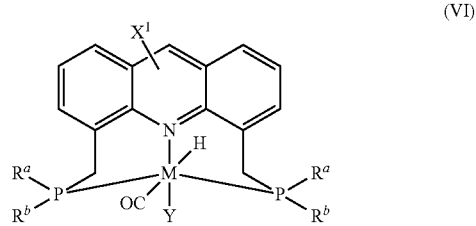

(VI)

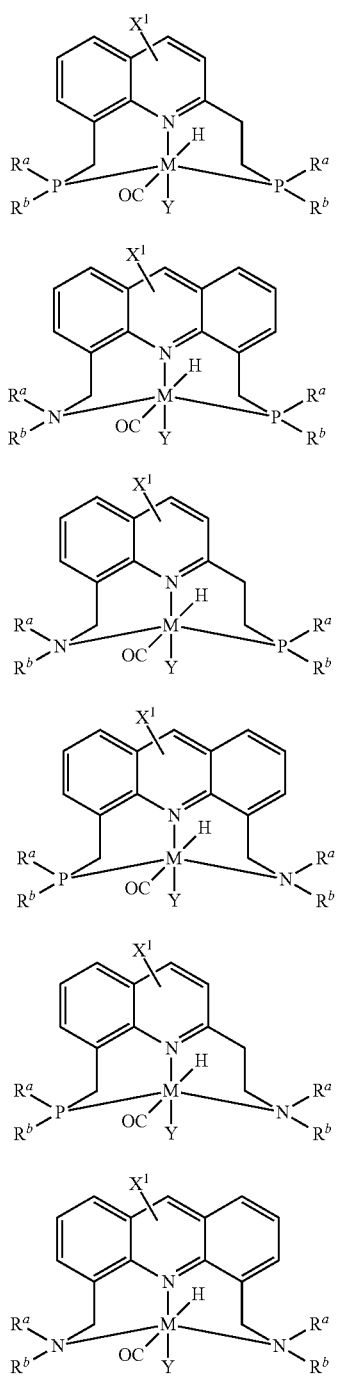

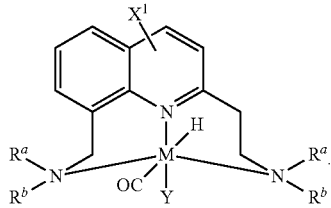

5. The process of claim 1, wherein the complex catalyst is a catalyst of formula (XIVb):

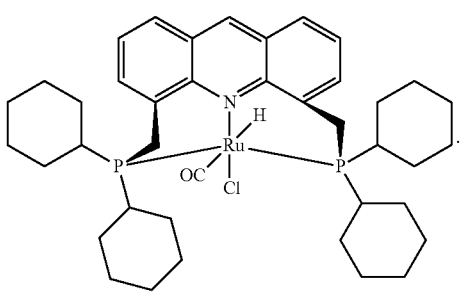

6. The process of claim 1, wherein, in formula (I), Y is F, Cl, or Br.

7. The process of claim 1, wherein, in formula (I), $L^3$ is CO.

8. The process of claim 1, wherein the aminating is carried out at a temperature of from 110 to 160° C. and a pressure of from 1 to 15 MPa.

9. The process of claim 1, wherein the diol is selected from the group consisting of 1,2-ethanediol, 1,3-propanediol, 1,4-butanediol, 2 methyl-1,3-propanediol, 2,2-dimethyl-1,3-propanediol, diethylene glycol, triethylene glycol, polyethylene glycols, polypropylene glycols such as 1,3-polypropylene glycol, polytetrahydrofuran, 2,5-(dimethanol)-furan and diethanolamine.

10. The process of claim 1, wherein, in formula (I), Y is F, Cl or Br.

11. The process of claim 10, wherein Y is Cl.

12. The process of claim 11, wherein, in formula (I), $L^3$ is CO.

* * * * *